United States Patent
Ogata

(10) Patent No.: US 10,130,249 B2
(45) Date of Patent: Nov. 20, 2018

(54) INSPECTION APPARATUS, IMAGE PROCESSING APPARATUS, METHOD OF OPERATING INSPECTION APPARATUS, IMAGE PROCESSING METHOD, AND RECORDING MEDIUM

(71) Applicant: CANON KABUSHIKI KAISHA, Tokyo (JP)

(72) Inventor: Naoko Ogata, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 105 days.

(21) Appl. No.: 15/134,694

(22) Filed: Apr. 21, 2016

(65) Prior Publication Data

US 2016/0317013 A1    Nov. 3, 2016

(30) Foreign Application Priority Data

May 1, 2015  (JP) ................................ 2015-094244
Feb. 24, 2016 (JP) ................................ 2016-033071

(51) Int. Cl.
*A61B 3/10* (2006.01)
*A61B 3/14* (2006.01)
(Continued)

(52) U.S. Cl.
CPC .......... *A61B 3/0025* (2013.01); *A61B 3/0008* (2013.01); *A61B 3/12* (2013.01);
(Continued)

(58) Field of Classification Search
CPC ....... A61B 3/1015; A61B 3/103; A61B 3/102; A61B 3/14; A61B 3/1216; A61B 5/7264;
(Continued)

(56) References Cited

U.S. PATENT DOCUMENTS 5,438,562 A  *  8/1995  Kobayashi ........... G11B 7/1356
                                                369/112.21
6,028,306 A     2/2000  Hayashi
(Continued)

FOREIGN PATENT DOCUMENTS

EP    2 053 442 A1    4/2009
EP    2 517 618 A2   10/2012
(Continued)

OTHER PUBLICATIONS

Yusufu N. Sulai, et al., "Visualization of retinal vascular structure and perfusion with a nonconfocal adaptive optics scanning light ophthalmoscope," J. Opt. Soc. Am. A, vol. 31, No. 3, Mar. 2014, pp. 569-579.

(Continued)

*Primary Examiner* — Brandi Thomas
(74) *Attorney, Agent, or Firm* — Fitzpatrick, Cella, Harper & Scinto

(57) ABSTRACT

An inspection apparatus, including: a measurement optics system configured to scan an object to be inspected with measuring light from a light source; a dividing unit, which is arranged at a position conjugate with the object to be inspected, and is configured to divide return light, being the measuring light returning from the object to be inspected, into a plurality of light beams; a photo-receiving unit configured to receive the plurality of light beams obtained by the division; a recording unit configured to record image data of the object to be inspected, which is based on a plurality of intensity signals output by the photo-receiving unit, and a division direction in which the return light is divided, the image data being associated with the division direction; and an analysis unit configured to analyze the image data based on the associated division direction.

31 Claims, 10 Drawing Sheets

(51) Int. Cl.
*A61B 3/00* (2006.01)
*A61B 3/12* (2006.01)

(52) U.S. Cl.
CPC .............. *A61B 3/1225* (2013.01); *A61B 3/14* (2013.01); *A61B 2560/0475* (2013.01)

(58) Field of Classification Search
CPC .......... A61B 5/0059; A61B 2560/0242; A61B 3/0025; A61B 3/0041; A61B 3/12; A61B 5/0022; A61B 5/0024; A61B 5/04008; A61B 5/0476; A61B 5/055; A61B 5/1114; A61B 5/117
USPC .................. 351/200, 204–206, 209–246
See application file for complete search history.

(56) References Cited

U.S. PATENT DOCUMENTS

2002/0047992 A1* 4/2002 Graves .................. G02B 26/06
351/212
2004/0032650 A1 2/2004 Lauer
2004/0262534 A1 12/2004 MacAulay et al.
2007/0146869 A1 6/2007 Lauer
2010/0182612 A1 7/2010 Yoshida et al.

FOREIGN PATENT DOCUMENTS

JP 2014-198224 A 10/2014
WO 2010/073655 A1 7/2010

OTHER PUBLICATIONS

Drew Scales, et al., "In Vivo Imaging of Human Cone Photoreceptor Inner Segments," Investigational Ophthalmology and Visual Science, vol. 55, No. 7, Jul. 2014, pp. 4244-4151.
Aug. 1, 2016 European Search Report in European Patent Appln. No. 16167432.0.

* cited by examiner

INSPECTION APPARATUS, IMAGE PROCESSING APPARATUS, METHOD OF OPERATING INSPECTION APPARATUS, IMAGE PROCESSING METHOD, AND RECORDING MEDIUM

BACKGROUND OF THE INVENTION

Field of the Invention

The present invention relates to an inspection apparatus such as an ophthalmic imaging apparatus to be used in ophthalmologic diagnosis and treatment, an image processing apparatus, a method of operating an inspection apparatus, an image processing method, and a recording medium.

Description of the Related Art

Scanning laser ophthalmoscopes (hereinafter referred to as "SLO apparatus"), which are ophthalmic imaging apparatuses utilizing the principle of confocal laser microscopes, are configured to perform raster scan on the fundus of an eye with laser light serving as measuring light to quickly acquire a two-dimensional image of the fundus of the eye that is high in resolution from the intensity of return light of the measuring light.

In SLO apparatus, the measuring light needs to form a minute spot on the fundus of the eye in order to improve lateral resolution. It is, however, difficult to improve resolution by simply increasing the beam diameter of the measuring light, due to the distortion of the spot shape from aberrations of the measuring light and the return light thereof that are caused on the eye being inspected.

To solve this, adaptive optics SLO apparatuses (hereinafter referred to as "AO-SLO apparatus") have been developed in recent years which incorporate an adaptive optics system configured to measure aberrations by the eye that is being inspected and to compensate for aberrations of the measuring light and the return light thereof that are caused on the eye being inspected, with the use of a wavefront compensation device. The development has made acquiring a two-dimensional image (AO-SLO image) high in resolution a realistic possibility.

On the other hand, for some site or tissue of the fundus of the eye whose image is to be acquired, a two-dimensional image is acquired by intentionally using a light flux that is nonconfocal with the image acquisition site of the fundus of the eye (a nonconfocal image), in an attempt to obtain information about the fundus tissue that cannot be obtained from a confocal image.

A nonconfocal AO-SLO apparatus proposed in JOSA A, VOL. 31, Issue 3, pp. 569-579 (2014) is configured to acquire a nonconfocal image of the fundus of the eye by dividing return light returning from the fundus of the eye into two or more beams on an image forming surface where the return light forms an image, entering the beams to their respective light sensors, calculating (differences among) signals of the light sensors, and imaging the fundus of the eye, in an attempt to improve the S/N ratio of the acquired two-dimensional image (blood vessel image). There is also a report in IOVS, 55, 4244-4251 (2014) of the result of using a similar imaging method in which an image of photoreceptor cells as typical eye cells was acquired that had image characteristics different from those of images observed with confocal optics systems of the related art.

Some images acquired with the nonconfocal AO-SLO apparatus described above have dependence on a particular direction in terms of sharpness, which takes form as, for example, sharpness variations between the left side and right side of a blood vessel in an acquired image. This is called the directionality of image characteristics. Taking the directionality of image characteristics into account is beneficial in an analysis of such images having the dependence. However, both of the documents cited above use an analysis method of the related art, for example, one in which pathological changes and the like of an eye to be inspected are evaluated simply by obtaining the size or density of eye cells (Japanese Patent Application Laid-Open No. 2014-198224), without taking into account the directionality of image characteristics. With this and other similar analysis methods of the related art, an image high in image characteristics dependence on a particular direction is analyzed as a nonconfocal image containing unsharp portions, which can make successful detection of, for example, photoreceptor cells difficult.

SUMMARY OF THE INVENTION

It is an object of the present invention to analyze image data of an object to be inspected with precision.

In order to solve the above-mentioned problem, according to one embodiment of the present invention, there is provided an inspection apparatus, including:

a measurement optics system configured to scan an object to be inspected with measuring light from a light source;

a dividing unit, which is arranged at a position conjugate with the object to be inspected, and is configured to divide return light, being the measuring light returning from the object to be inspected, into a plurality of light beams;

a photo-receiving unit configured to receive the plurality of light beams obtained by the division;

a recording unit configured to record image data of the object to be inspected, which is based on a plurality of intensity signals output by the photo-receiving unit, and a division direction in which the return light is divided, the image data being associated with the division direction; and an analysis unit configured to analyze the image data based on the associated division direction.

According to the present invention, an image can be analyzed taking into account return light division directions that correspond to the directionality of image characteristics. That is, an image analysis in consideration of the directionality of image characteristic can be executed. As the result, image data of an object to be inspected can also be analyzed with precision.

Further features of the present invention will become apparent from the following description of exemplary embodiments with reference to the attached drawings.

DESCRIPTION OF THE EMBODIMENTS

A mode for carrying out the present invention is now described by way of the following embodiment. Note that, the embodiment described below does not restrict the present invention as set forth in the appended claims, and not all of the combinations of the features described in the embodiment are essential to the solution of the present invention.

The present invention is based on findings that, in a nonconfocal AO-SLO image acquired with a nonconfocal AO-SLO apparatus, the directionality of image characteristics described above is often dependent on directions in which return light used to acquire the image is divided. According to the present invention, image analysis that takes into account image characteristics dependent on directions in which a flux of return light returning from the fundus of the eye is divided can be executed by recording the division directions and an acquired image in association with each other and utilizing the information about the division directions when image processing and analysis are performed on the acquired image.

An embodiment of the present invention is described.

An inspection apparatus according to the embodiment includes an AO-SLO apparatus that includes an adaptive optics system for acquiring a fine two-dimensional image despite optical aberrations of an eye to be inspected, and that is capable of picking up a high-resolution, two-dimensional image (AO-SLO image) of the fundus of the eye to be inspected which is an image acquisition target, in particular, a nonconfocal image of the fundus of the eye. The inspection apparatus is also provided with a WF-SLO apparatus, an anterior ocular segment observation device, and a fixation lamp displaying device. The WF-SLO apparatus picks up a two-dimensional image that is wider in field angle (a WF-SLO image) for the purpose of aiding the acquisition of an AO-SLO image. The anterior ocular segment observation device is used to grasp the incident position of measuring light. The fixation lamp displaying device is used to guide the line of sight in order to adjust where an image is picked up.

In this case, in order to pick up a two-dimensional image high in resolution, the apparatus includes the adaptive optics system. However, the adaptive optics system may not be included as long as the configuration of the optical system can realize high resolution.

<Overall Configuration of Apparatus>

Figure 1A:
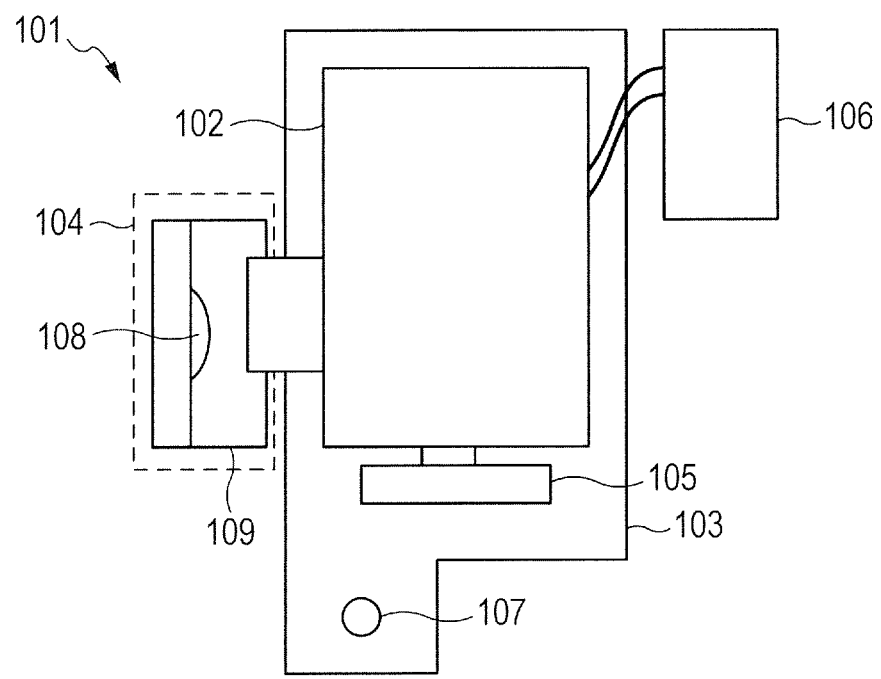
FIG. 1A is a plan view for illustrating the overall configuration of an SLO apparatus according to an embodiment of the present invention.
Figure 1B:
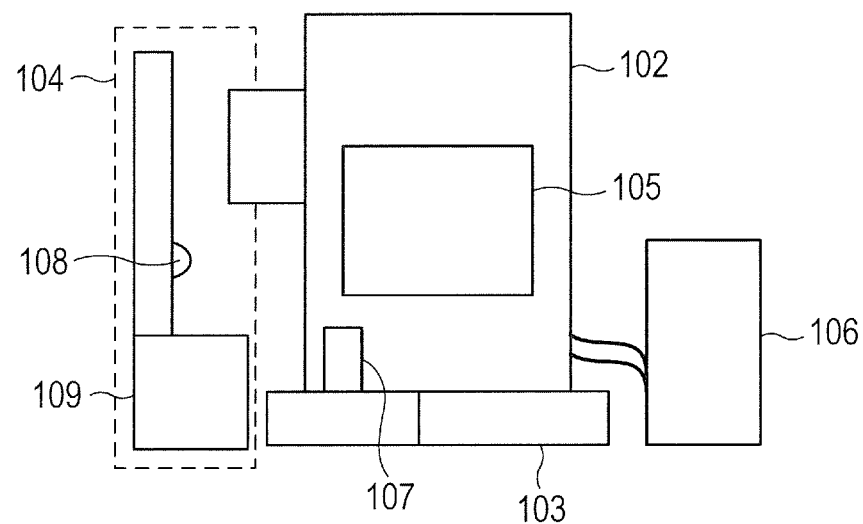
FIG. 1B is a side view thereof.

First, a schematic configuration of an AO-SLO apparatus 101 according to this embodiment is described specifically with reference to FIG. 1A and FIG. 1B. FIG. 1A is a plan view of the AO-SLO apparatus 101 viewed from above. FIG. 1B is a side view of the AO-SLO apparatus 101 viewed from a side.

The AO-SLO apparatus 101 roughly includes a head unit 102, a stage unit 103, a face rest unit 104, a liquid crystal monitor 105, and a control PC 106. The head unit 102 has a main optics system built inside. The stage unit 103 moves the head unit 102 in horizontal and vertical directions. The face rest unit 104 is where a subject puts his/her face, and is used to adjust the position of the face. The liquid crystal monitor 105 is configured to display an operation screen. The control PC 106 handles overall control of the AO-SLO apparatus 101, and has an image processing apparatus 600 built inside which is described later with reference to FIG. 6.

The head unit 102 is arranged on the stage unit 103 and can be moved in a horizontal direction (a direction parallel to the drawing sheet of FIG. 1A) by tilting a joystick 107, and in a vertical direction (a direction perpendicular to the drawing sheet of FIG. 1A) by rotating the joystick 107. The face rest unit 104 includes a chin rest 108 on which the chin of a subject is put, and a chin rest drive unit 109 configured to move the chin rest 108 by way of an electric stage.

<Optics System Configuration>

Figure 2A:
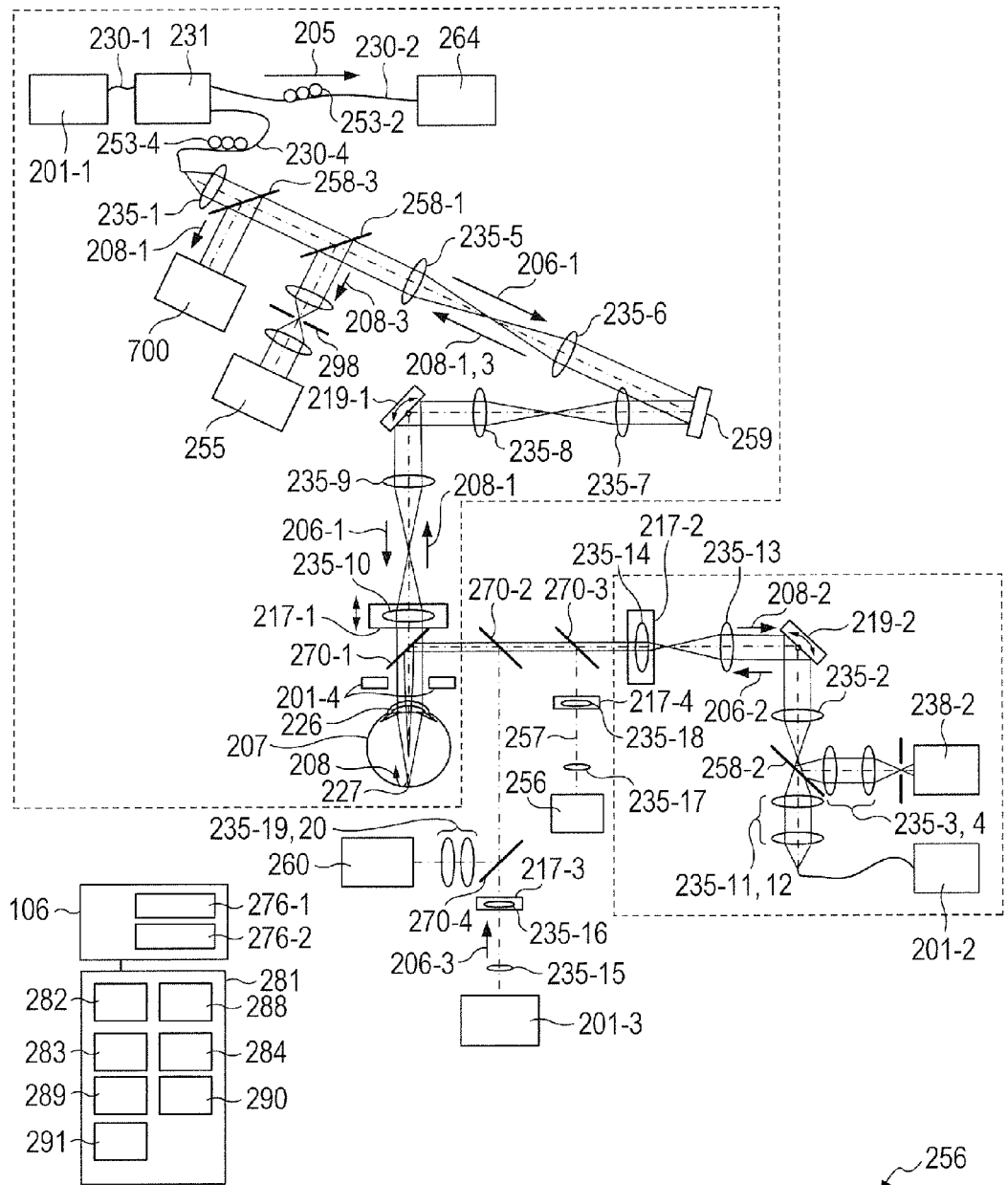
FIG. 2A is a diagram for illustrating the configuration of an optics system of the SLO apparatus according to the embodiment of the present invention.

A specific description is given next on the optics system built inside the head unit 102, with reference to FIG. 2A. The optics system described below, in particular, an AO-SLO unit, serves in this embodiment as a measurement optics system configured to scan an object to be inspected with measuring light from a light source.

Light exiting a light source 201-1 is divided by an optical coupler 231 into reference light 205 and measuring light 206-1. The measuring light 206-1 is led to a measurement optics system with the use of a single-mode fiber 230-4, and reaches an XY scanner 219-1 through a collimator lens 235-1 and a spatial light modulator 259. The measuring light emitted by the XY scanner 219-1 for scanning is led to a fundus 227 of an eye-to-be-inspected 207, which is an object to be observed and inspected, through an objective lens 235-10 with a focus function, a dichroic mirror 270-1, and others. The objective lens 235-10 is capable of compensating for an ametropia value of the eye to be inspected. A fixation lamp 256 is configured to emit a light flux 257, which is coupled to the measuring optics system through the dichroic mirror 270-1. With the fixation lamp 256, the subject is prompted to fix or rotate the line of sight of the eye-to-be-inspected 207.

Figure 8:
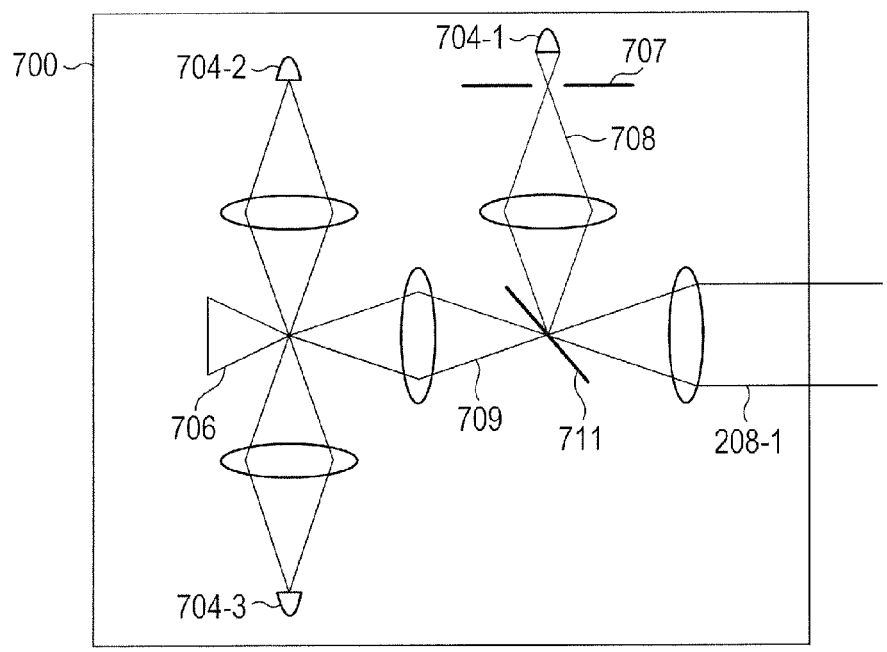
FIG. 8 is a diagram for illustrating the configuration of a photo-receiving unit of the SLO apparatus according to the embodiment of the present invention.
Figure 9:
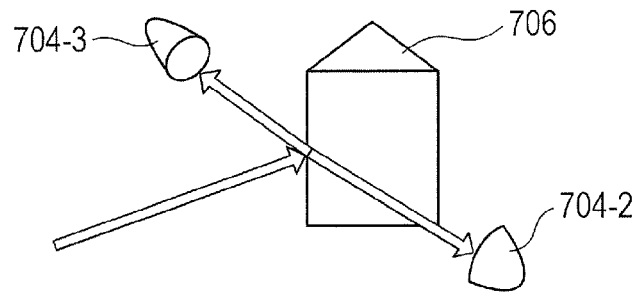
FIG. 9 is a diagram for illustrating the configuration of a second light flux dividing unit of the SLO apparatus according to the embodiment of the present invention

The measuring light 206-1 is reflected or scattered by the fundus 227 of the eye to be inspected to turn into return light 208. The return light 208 travels back the optical path to be reflected by a beam splitter 258-3, and the reflected light enters detectors 704-1 to 704-3 (see FIG. 8), which serve as a photo-receiving unit 700. The detectors 704-1 to 704-3 are configured to convert the light intensity of return light 208-1 into a voltage, and a signal having the voltage is used to form a two-dimensional image of the eye-to-be-inspected 207. In this embodiment, the entire optical system is mainly formed of a refracting optical system using lenses. However, it is also possible to form the optical system by using a reflecting optical system using spherical mirrors instead of the lenses.

In addition, a reflective spatial light modulator is used as an aberration compensation device in this embodiment, but it is also possible to use a transmissive spatial light modulator or a variable shape mirror.

<Light Source of AO-SLO Unit>

Next, details of the light source 201-1 are described. The light source 201-1 is a super luminescent diode (SLD) serving as a typical low-coherent light source. Light acquired by the SLD has a wavelength of 840 nm and a bandwidth of 50 nm. In this case, in order to acquire a two-dimensional image having little speckle noise, a low-coherent light source is selected. Further, although the SLD is selected as the light source in this embodiment, any type of light source may be used as long as the light source can emit low-coherent light. For example, an amplified spontaneous emission (ASE) light source may be used.

In view of the measurement of the eye, a suitable wavelength is a near infrared light wavelength. The wavelength affects the lateral resolution of the acquired two-dimensional image, and hence the wavelength is desired to be as short as possible. Therefore, in this embodiment, the wavelength is set to 840 nm. Another wavelength may be selected depending on a measurement site that is an object to be observed.

The light exiting the light source 201-1 is led to the optical coupler 231 through a single-mode fiber 230-1 and is divided into the reference light 205 and the measuring light 206-1 in a ratio of 90:10. Polarization controllers 253-2 and 253-4 are arranged on the respective optical fibers.

<Reference Light Optical Path of AO-SLO Unit>

Next, an optical path of the reference light 205 is described.

The reference light 205 divided by the optical coupler 231 enters a light intensity measuring apparatus 264 through an optical fiber 230-2. The light intensity measuring apparatus 264 is used for measuring light intensity of the reference light 205 so as to monitor the light intensity of the measuring light 206-1.

<Measuring Light Optical Path of AO-SLO Unit>

Next, an optical path of the measuring light 206-1 is described.

The measuring light 206-1 divided by the optical coupler 231 is led to the collimator lens 235-1 through the single-mode fiber 230-4, and is adjusted to be a collimated light beam having a beam diameter of 4 mm.

The measuring light 206-1 passes through the beam splitter 258-3, a beam splitter 258-1, and lenses 235-5 and 235-6 and enters the spatial light modulator 259.

In this case, the spatial light modulator 259 is controlled by the control PC 106 via a spatial light modulator driver 288 included in a driver unit 281.

Next, the measuring light 206-1 is modulated by the spatial light modulator 259, passes through lenses 235-7 and 235-8, and enters a mirror of the XY scanner 219-1. For simplification of the illustration, the XY scanner 219-1 is illustrated as a single mirror. However, in an actual case, two mirrors, that is, an X scanner and a Y scanner, are arranged close to each other so as to raster-scan the fundus 227 in a direction perpendicular to the optical axis. The center of the measuring light 206-1 on the optical axis is adjusted to match each center of rotation of the mirrors of the XY scanner 219-1.

The X scanner is a scanner configured to scan the measuring light 206-1 in the direction parallel to the drawing sheet, and a resonance type scanner is used for the X scanner here. The drive frequency is approximately 7.9 kHz. In addition, the Y scanner is a scanner configured to scan the measuring light 206-1 in the direction perpendicular to the drawing sheet, and a galvano scanner is used for the Y scanner here. The drive waveform is a sawtooth wave, the frequency is 32 Hz, and the duty ratio is 16%. The drive frequency of the Y scanner is an important parameter for determining a frame rate of the AO-SLO image acquisition.

The XY scanner 219-1 is controlled by the control PC 106 via an optical scanner driver 282 included in the driver unit 281. The XY scanner 219-1 is configured to scan the measuring light 206-1 from the light source 201-1 on the fundus 227 of the eye to be inspected, which is the object to be inspected, in the measurement optical system.

A lens 235-9 and the objective lens 235-10 correspond to an optical system configured to scan the fundus 227 in a depth direction and serve to scan the fundus 227 with the measuring light 206-1 in a manner of pivoting on the center of a pupil of the eye-to-be-inspected 207.

The beam diameter of the measuring light 206-1 is mm in this embodiment, but the beam diameter may be larger than 4 mm in order to acquire an optical image higher in resolution.

Further, an electric stage 217-1 supporting the objective lens 235-10 can move in a direction indicated by the arrows so as to move the position of the accompanying objective lens 235-10, to thereby perform focus adjustment.

The electric stage 217-1 is controlled by the control PC 106 through an electric stage driver 283 included in the driver unit 281.

The position of the objective lens 235-10 may be adjusted, to thereby focus the measuring light 206-1 to a predetermined layer of the fundus 227 of the eye-to-be-inspected 207 to observe the layer. In addition, it is possible to support the case where the eye-to-be-inspected 207 has ametropia.

The measuring light 206-1 enters the eye-to-be-inspected 207 and is reflected and scattered by the fundus 227 that is the object to be inspected so as to be the return light 208, which enters the photo-receiving unit 700. The incident return light 208-1 is split by a dividing unit, which is described later, and beams created by the split separately reach the detectors 704-1 to 704-3, which are a photo-receiving unit. Highly sensitive and high speed light sensors such as avalanche photodiodes (APDs) and photomultiplier tubes (PMTs) are used for the detectors 704-1 to 704-3. Each of the detectors outputs an intensity signal indicating the intensity of a light flux received by the detector.

<Photo-receiving Unit>

The schematic configuration of the photo-receiving unit 700 is described next with reference to FIG. 7A to FIG. 9 and FIG. 12A to FIG. 13.

The return light 208-1 is divided and partially reflected by a partially reflecting mirror 711, which is a first light flux dividing unit placed on an image forming surface that is a plane substantially conjugate with the fundus 227 of the eye to be inspected. Out of the beams created by the division, reflected light 708 passes through a pinhole 707 formed in the image forming surface and enters the detector 704-1. With this configuration, fundus image data for forming a fundus image with a confocal optics system and for displaying the formed image is obtained from an output of the detector 704-1 and from a scanning signal used at the time the data is obtained. An image acquisition mode in which confocal image data used to form and display the confocal image is obtained is referred to as "second image acquisition mode". Specifically, the partially reflecting mirror 711, which is a light flux dividing unit placed on a plane conjugate with the fundus of the eye to be inspected divides return light returning from the eye to be inspected into two or more light fluxes (light beams).

Figure 7A:
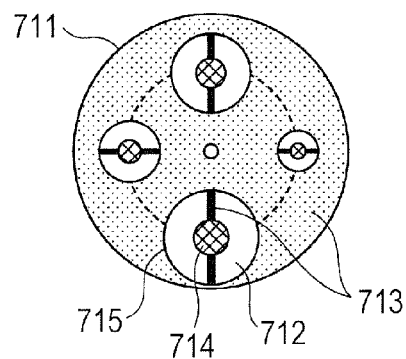
FIG. 7A is a diagram for illustrating the configuration of a first light flux dividing unit of the SLO apparatus according to the embodiment of the present invention.

The other partial light 709 enters the partially reflecting mirror 711 passes through a transmission region 712, which is outside the central portion of a division pattern 715 illustrated in FIG. 7A, and is divided further into two light fluxes by a light flux dividing prism 706, which is placed on an image forming surface, in order to form a nonconfocal image. The two light fluxes after the division are received by the detectors 704-2 and 704-3, respectively, and each of the detectors outputs a voltage signal that reflects the intensity of the received light flux. The configurations are illustrated stereoscopically in FIG. 9. The detectors 704-2 and 704-3 are each coaxially aligned with the scanning direction of the X scanner. The voltage signals output by the respective detectors are converted into digital values by an AD board 276-1 included in the control PC 106, and the digital values are input to the control PC 106.

When digital values that are obtained from light beams entering the detectors 704-2 and 704-3 at one point in time are given as Ia and Ib, the following expression is used to obtain a pixel value I that a nonconfocal image has when the division direction is the X-direction, namely, fundus image data for forming the nonconfocal image.

$$I = \frac{Ia - Ib}{Ia + Ib}$$

A mode in which an image generated from the pixel value I in the X-direction is used to obtain a nonconfocal image when the division direction is the X-direction is a first image acquisition mode. An image acquired with the AO-SLO apparatus usually has characteristics in a direction corresponding to a direction in which a light flux is divided by the light flux dividing prism 706, i.e., directionality of image characteristics. The AO-SLO apparatus records in a recording device the value of I and the scanning direction of the X scanner as information about the direction of the light flux division, in other words, a rotation angle with respect to the optical axis of the light flux dividing prism 706, along with an image picked up in the first image acquisition mode. Details of this step are described later.

Figure 7B:
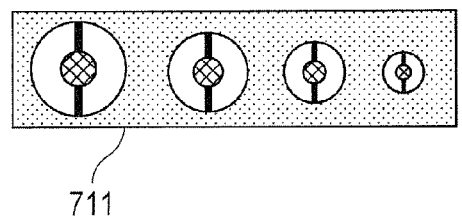
FIG. 7B is a diagram for illustrating another configuration of the first light flux dividing unit.

The partially reflecting mirror 711 includes a reflection region 714 at a central portion, the transmission region 712 placed outside the reflection region 714, and a light shielding region 713, which defines the transmission region 712 by blocking light. As illustrated in FIG. 7A and FIG. 7B, the partially reflecting mirror 711 may have a plurality of division patterns 715 each of which is a set of the thus arranged reflection region 714, transmission region 712, and light shielding region 713. The center of each division pattern is positioned at the center of the optical axis of the return light 208. The partially reflecting mirror 711 has an elliptical shape that gives a circular shape to each division pattern viewed from the optical axis direction when the partially reflecting mirror 711 is arranged obliquely with respect to the optical axis of the return light 208. The partially reflecting mirror 711 is controlled by a division pattern selection control unit 289 so that division patterns are selectively switched.

Examples of switching the division patterns 715 are illustrated in FIG. 7A and FIG. 7B. In the switching examples, the light flux dividing prism 706, which is the second light flux dividing unit, divides a light flux invariably into two, and the size of beams created by the division is varied by switching the division patterns 715. The switching has the following effects. Specifically, when a division pattern in which the reflection region 714 is small in diameter is selected, the focal depth decreases and the contrast increases, but the signal-to-noise ratio drops. When a division pattern in which the reflection region 714 is large in diameter is selected, on the other hand, the focal depth increases and the contrast drops, but the signal-to-noise ratio is relatively high. An adjustment that gives an image a favorable contrast and signal-to-noise ratio can thus be made by switching division patterns selectively.

Figure 12A:
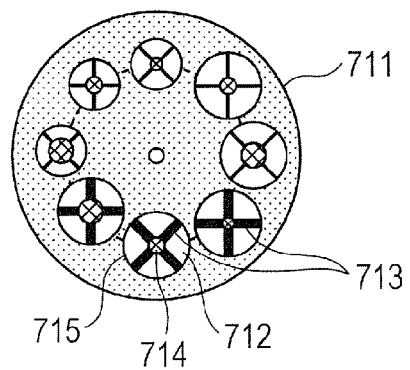
FIG. 12A, FIG. 12B and FIG. 12C are each a diagram for illustrating a different configuration of the first light flux dividing unit of the SLO apparatus according to the embodiment of the present invention.
Figure 12B:
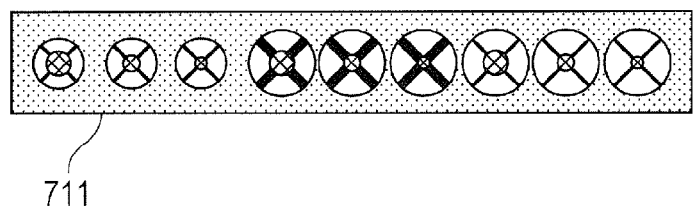
Figure 12C:
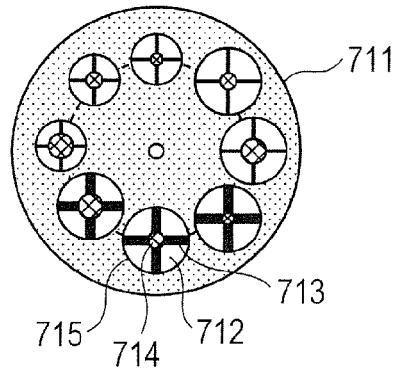
Figure 13:
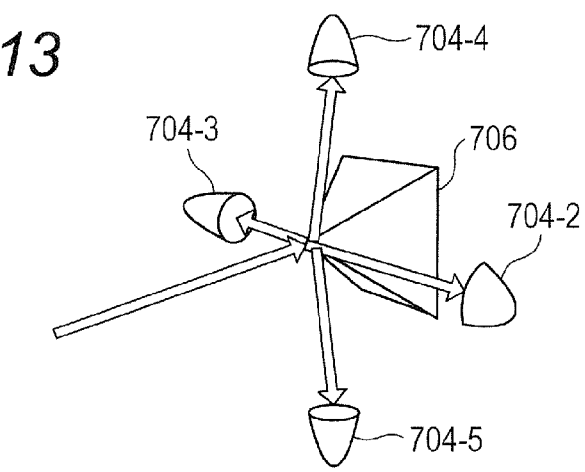
FIG. 13 is a diagram for illustrating another configuration of the second light flux dividing unit of the SLO apparatus according to the embodiment of the present invention.

The partially reflecting mirror 711 may be a light shielding plate on which different division patterns are arranged in a circle as illustrated in FIG. 7A, and which is rotated mechanically to select one of the division patterns. Alternatively, the partially reflecting mirror 711 may be a light shielding plate on which a plurality of division patterns are aligned in a single file as illustrated in FIG. 7B, and which is slid mechanically to select one of the division patterns. The partially reflecting mirror 711 may also be as illustrated in FIG. 12A to FIG. 12C, for example. In detail, the number into which light is divided may be raised to four as illustrated in FIG. 12A, and division patterns varied in the direction of division, in the width of the light shielding region, which divides the transmission region, and in the size of the reflection region may be arranged on a single reflective plate that can be rotated. Detectors corresponding to beams that are created by dividing a light flux need to be arranged in directions in which the light flux is divided. It is therefore preferred to vary patterns based on what image is to be acquired, such as keeping only the division direction constant as illustrated in FIG. 12B when the number and arrangement of detectors used are constant. The division patterns may of course be arranged in a straight line instead of a circle. In short, the method or mode of blocking the path of light to the photo-receiving unit is not limited to the ones described here.

The division direction described here is a direction perpendicular to a direction in which the light shielding region 713 dividing the transmission region 712 stretches. In the example of FIG. 7B, a light flux is divided into beams on the left side and right side of the drawing sheet in every division pattern. In the case of FIG. 12B, a light flux is divided left to right and top to bottom into four beams. In the case of FIG. 12C, a light flux is divided top to bottom, that is, in a lower left to upper right direction and upper left to lower right direction into four beams.

A drive unit configured to rotate the light flux dividing prism and the two detectors about the branching point may be provided to rotate the light flux dividing prism and the detectors manually or automatically with respect to the optical axis of the light 709. This configuration enables the AO-SLO apparatus 101 to acquire a nonconfocal image that uses a light flux divided in a particular direction (angle) with respect to the scanning direction of the X scanner by changing the direction in which the light is branched by the light flux dividing prism. For example, in the case where an object for which image acquisition and analysis are to be performed is a particular blood vessel, setting the light flux division direction to a direction perpendicular to the running direction of the target blood vessel is desirable in order to obtain a nonconfocal image in which the characteristics of the blood vessel are emphasized. In this case, the AO-SLO apparatus 101 of this embodiment is capable of analyzing an image by obtaining a signal divided in an arbitrary direction with respect to the scanning direction of the X scanner.

The number of directions in which a light flux is divided by the light flux dividing prism is not limited to two. For example, a signal divided in an arbitrary direction can be obtained without a rotatable drive unit by using a quadrangular pyramid prism for the light flux dividing prism and providing four detectors 704-2 to 704-5 as in FIG. 13. Specifically, digital values obtained with four detectors can be combined in an arbitrary direction at an arbitrary proportion to obtain a pixel value divided in an arbitrary direction through calculation. In this embodiment, the detectors each serve as a photo-receiving unit configured to receive a light flux that is created by dividing another light flux and to output an intensity signal that indicates the intensity of the received light flux.

The number of detectors, the number into which light is divided, and the method of division or the manner of setting directions are not limited to the ones described above, as long as the number and direction of division can be set by an arbitrary method. The AO-SLO apparatus 101 in this case calculates an arbitrary division direction that is obtained through calculation, and records in the recording device the calculated direction, instead of recording the exact rotation angle of the light flux dividing prism which is described above, along with a nonconfocal image picked up in the first image acquisition mode. In other words, an image acquisition mode is recorded in the recording device in association with an image.

<Overall WF-SLO Unit>

Next, a WF-SLO unit is described with reference to FIG. 2A.

The WF-SLO unit basically has the same configuration as that of the AO-SLO unit. Overlapping description of the same part is omitted.

Light exiting a light source 201-2 is led to the eye-to-be-inspected 207, which is an object to be observed, through a lens 235-2, lenses 235-11 to 235-13, a focusing lens 235-14, an XY scanner 219-2, the dichroic mirror 270-1, dichroic mirrors 270-2 and 270-3, and others. The light source 201-2 is an SLD as in the light source of the AO-SLO unit, and emits light having a wavelength of 920 nm and a bandwidth of 20 nm.

<Measuring Light Optical Path of WF-SLO Unit>

Next, an optical path of measuring light 206-2 is described.

The measuring light 206-2 exiting the light source 201-2 is led to the eye-to-be-inspected 207 that is an object to be observed through the lenses 235-2 and 235-11 to 235-14, the XY scanner 219-2, the dichroic mirror 270-1, and others.

An X scanner that is a component of the XY scanner 219-2 is a scanner configured to scan the measuring light 206-2 in the direction parallel to the drawing sheet, and a resonance type scanner is used for the X scanner here. The drive frequency is approximately 3.9 kHz. In addition, a Y scanner that is a component of the XY scanner 219-2 is a scanner configured to scan the measuring light 206-2 in the direction perpendicular to the drawing sheet, and a galvano scanner is used for the Y scanner here. The drive waveform is a sawtooth wave, the frequency is 15 Hz, and the duty ratio is 16%. The drive frequency of the Y scanner is an important parameter for determining a frame rate of the WF-SLO image.

The beam diameter of the measuring light 206-2 is 1 mm, but may be larger than 1 mm in order to acquire an optical image higher in resolution.

The measuring light 206-2 enters the eye-to-be-inspected 207 and is reflected or scattered by the fundus 227 so as to be return light. The return light reaches a detector 238-2 through the dichromic mirrors 270-1 to 270-3, the lenses 235-13 and 235-14, the lens 235-2, lenses 235-3 and 235-4, the XY scanner 219-2, a beam splitter 258-2, and others.

<Description of Beacon Unit>

Next, a beacon unit configured to measure aberrations generated in the eye-to-be-inspected 207 is described.

Measuring light 206-3 exiting a light source 201-3 is led to the eye-to-be-inspected 207 that is an object to be observed through a lens 235-15, a focusing lens 235-16, a dichroic mirror 270-4, and others. In this case, the measuring light 206-3 enters the eye-to-be-inspected 207 under a state of being decentered from the center of the eye-to-be-inspected 207 in order to avoid being reflected from a cornea 226. Part of return light 208-3 enters, through the beam splitter 258-1 and a pinhole 298, a wavefront sensor 255, where aberrations of the return light 208-3 which are generated in the eye-to-be-inspected 207 are measured. In this case, the pinhole 298 is formed for the purpose of shielding unnecessary light other than the return light 208-3. The wavefront sensor 255 is electrically connected to the control PC 106. The wavefront sensor 255 is a Shack-Hartmann wavefront sensor, and the measurement range thereof is set to from −10 D to +5 D. The obtained aberration is expressed through use of the Zernike polynomials and indicates the aberration of the eye-to-be-inspected 207. The Zernike polynomials include the following terms: tilt, defocus, astigmatism, coma, trefoil, and the like. The light source 201-3 has a center wavelength of 760 nm and a wavelength width of 20 nm.

In this case, the lenses 235-5 to 235-10 and the like are arranged so that the cornea 226, the XY scanner 219-1, the wavefront sensor 255, and the spatial light modulator 259 are optically conjugate to each other. Therefore, the wavefront sensor 255 can measure the aberrations of the eye-to-be-inspected 207. In addition, the spatial light modulator 259 can correct the aberrations of the eye-to-be-inspected 207.

<Fixation Lamp Unit>

Figure 2B:
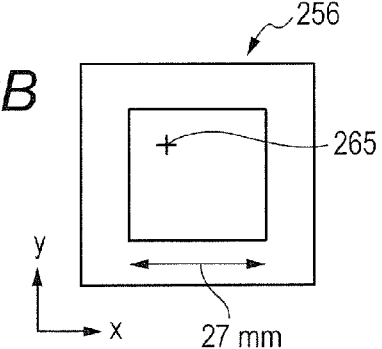
FIG. 2B is a diagram for illustrating a fixation lamp displaying surface.

The fixation lamp 256 is formed of a light-emitting display module and has a display surface (27 mm×27 mm, 128 pixels×128 pixels) on an XY-plane. In this case, a liquid crystal, an organic EL, an LED array, or the like can be used as the fixation lamp 256. When the eye-to-be-inspected 207 watches a light flux 257 from the fixation lamp 256, the eye-to-be-inspected 207 is prompted to fixate or rotate. On the display surface of the fixation lamp 256, for example, a cross-shaped pattern is displayed so as to blink at any lighting position 265 as illustrated in FIG. 2B.

The light flux 257 from the fixation lamp 256 is led to the fundus 227 through lenses 235-17 and 235-18, and the dichroic mirrors 270-1 to 270-3. Further, the lens 235-17 and a focusing lens 235-18 are arranged so that the display surface of the fixation lamp 256 and the fundus 227 are optically conjugate to each other. Further, the fixation lamp 256 is controlled by the control PC 106 via a fixation lamp driver 284 included in the driver unit 281.

<Anterior Ocular Segment Observation Unit>

Next, the anterior ocular segment observation unit is described.

Light output from an anterior ocular segment illumination light source (light source) 201-4 illuminates the eye-to-beinspected 207. The light reflected from the eye-to-be-inspected 207 enters a CCD camera 260 through the dichroic mirrors 270-1, 270-2, and 270-4, and lenses 235-19 and 235-20. The light source 201-4 is an LED having a center wavelength of 740 nm.

<Focus, Shutter, and Astigmatism Correction>

As described above, the optical system built in the head unit 102 includes the AO-SLO unit, the WF-SLO unit, the beacon unit, the fixation lamp unit, and the anterior ocular segment observation unit. Of those, the AO-SLO unit, the WF-SLO unit, the beacon unit, and the fixation lamp unit have the electric stages 217-1 to 217-4 described above, respectively and individually, and are configured to move the four electric stages 217-1 to 217-4 in a coordinated manner, respectively. Note that, in the case where a focus position is intended to be adjusted individually, the electric stages can also be moved individually for adjustment.

Further, the AO-SLO unit, the WF-SLO unit, and the beacon unit each include a shutter (not shown), and whether or not the measuring light is caused to enter the eye-to-be-inspected 207 can be controlled by opening or closing the shutter. The shutter is used here, but whether or not the measuring light is caused to enter the eye-to-be-inspected 207 can also be controlled by directly turning on/off the light sources 201-1 to 201-3. Similarly, the anterior ocular segment observation unit and the fixation lamp unit can also be controlled by turning on/off the light source 201-4 and the fixation lamp 256.

Further, the objective lens 235-10 can be replaced, and a spherical lens or a cylindrical lens may be used in accordance with the aberration (ametropia) of the eye-to-be-inspected 207. Further, the number of the lenses is not limited to one, and a plurality of lenses may be combined and arranged.

<Wavelength>

Figure 3:
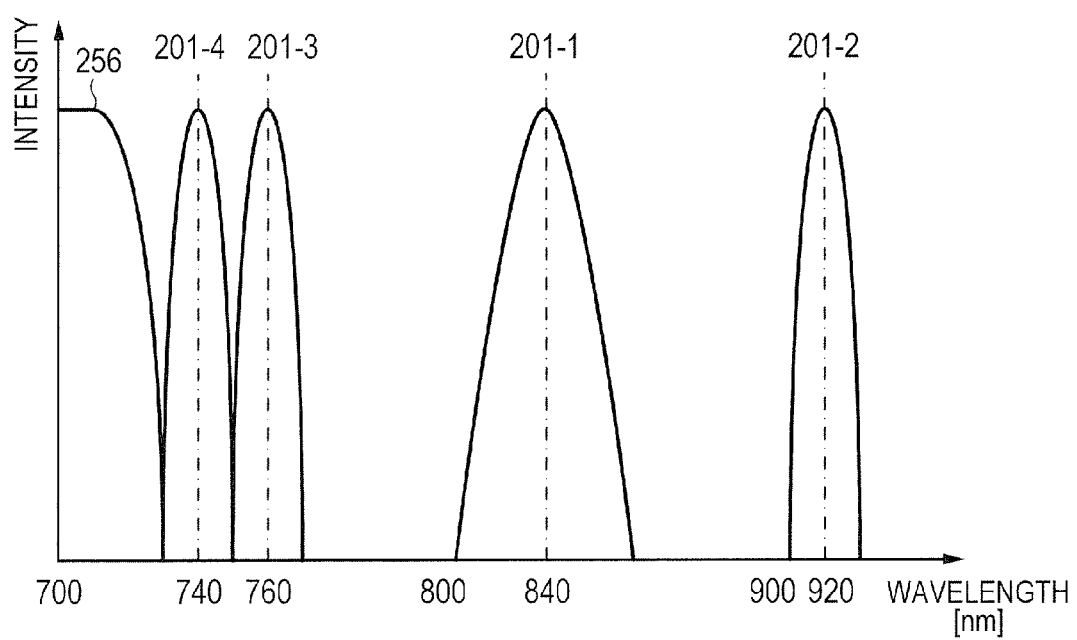
FIG. 3 is a graph for showing a measuring light wavelength distribution of the SLO apparatus according to the embodiment of the present invention.

The wavelength distribution of light beams exiting the light sources used in the AO-SLO unit, the WF-SLO unit, the beacon unit, the fixation lamp unit, and the anterior ocular segment observation unit is shown in FIG. 3. In order to separate the light beams by the dichroic mirrors 270-1 to 270-4, the light beams are set to have different wavelength bands. Note that, the difference in wavelength of the respective light beams is shown in FIG. 3, and the intensity and spectrum shape are not defined therein.

<Imaging>

Next, a method of forming a picked up image is described.

The intensity of light incident on the detectors 704-1 to 704-3 is converted into a voltage. Voltage signals output by the detectors 704-1 to 704-3 are converted into digital values by the AD board 276-1 included in the control PC 106. The digital values are processed on the control PC 106 through data processing synchronized with the operating frequency or drive frequency of the XY scanner 219-1 to form an AO-SLO image. The AD board 276-1 takes in a signal at a rate of 15 MHz. Similarly, a voltage signal output by the detector 238-2 is converted into a digital value by an AD board 276-2 included in the control PC 106, and a WF-SLO image is formed from the digital value. In this embodiment, the AD boards serve as image forming units configured to form an image based on outputs of the respective detectors and a scanning signal of the measurement optics system.

<Image Acquisition Procedure>

Next, an image acquisition procedure in the AO-SLO apparatus 101 according to this embodiment is described with reference to FIG. 4 and FIG. 5.

Figure 4:
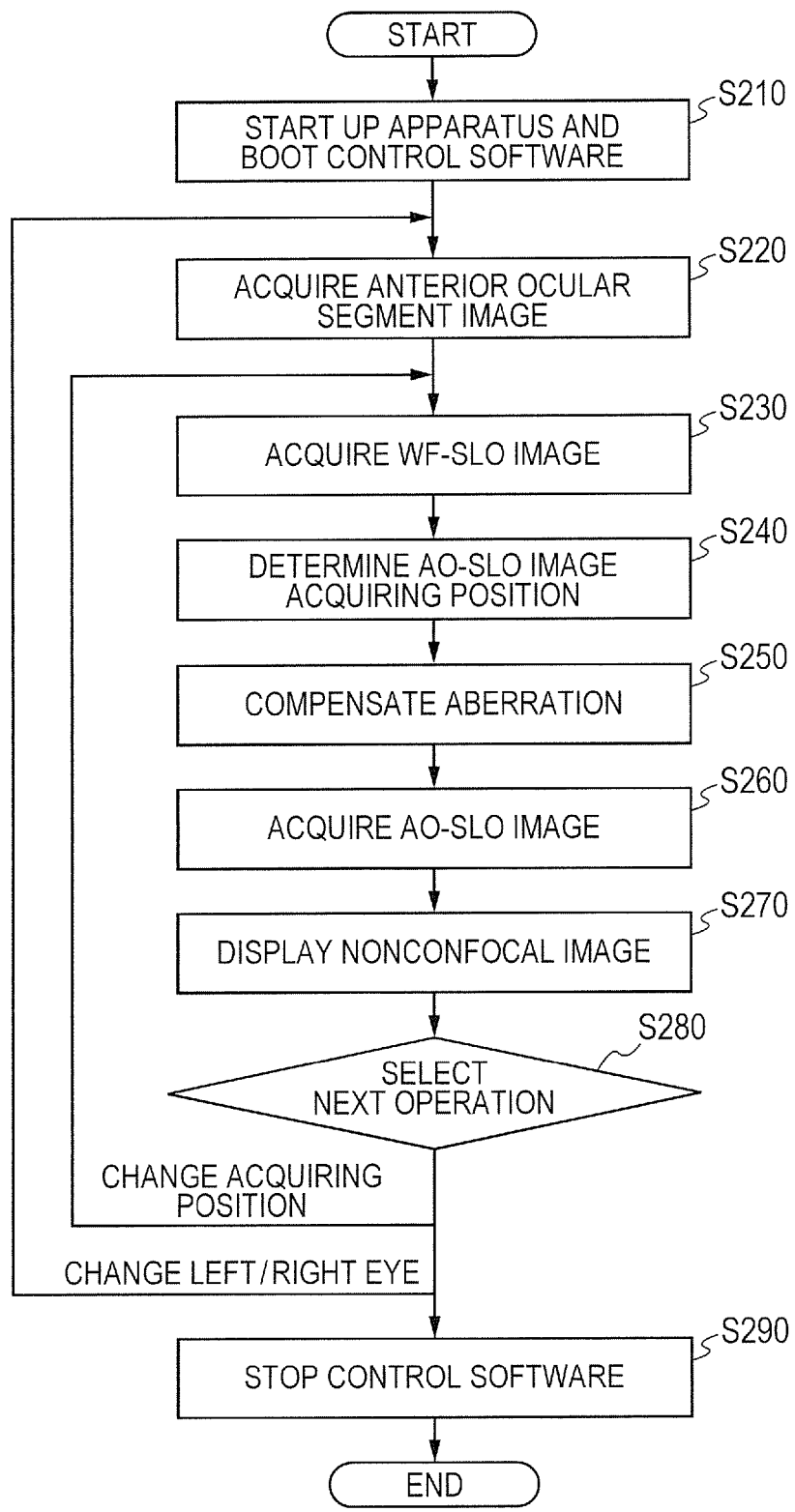
FIG. 4 is a diagram for illustrating an image acquisition procedure executed by the SLO apparatus according to the embodiment of the present invention.
Figure 5:
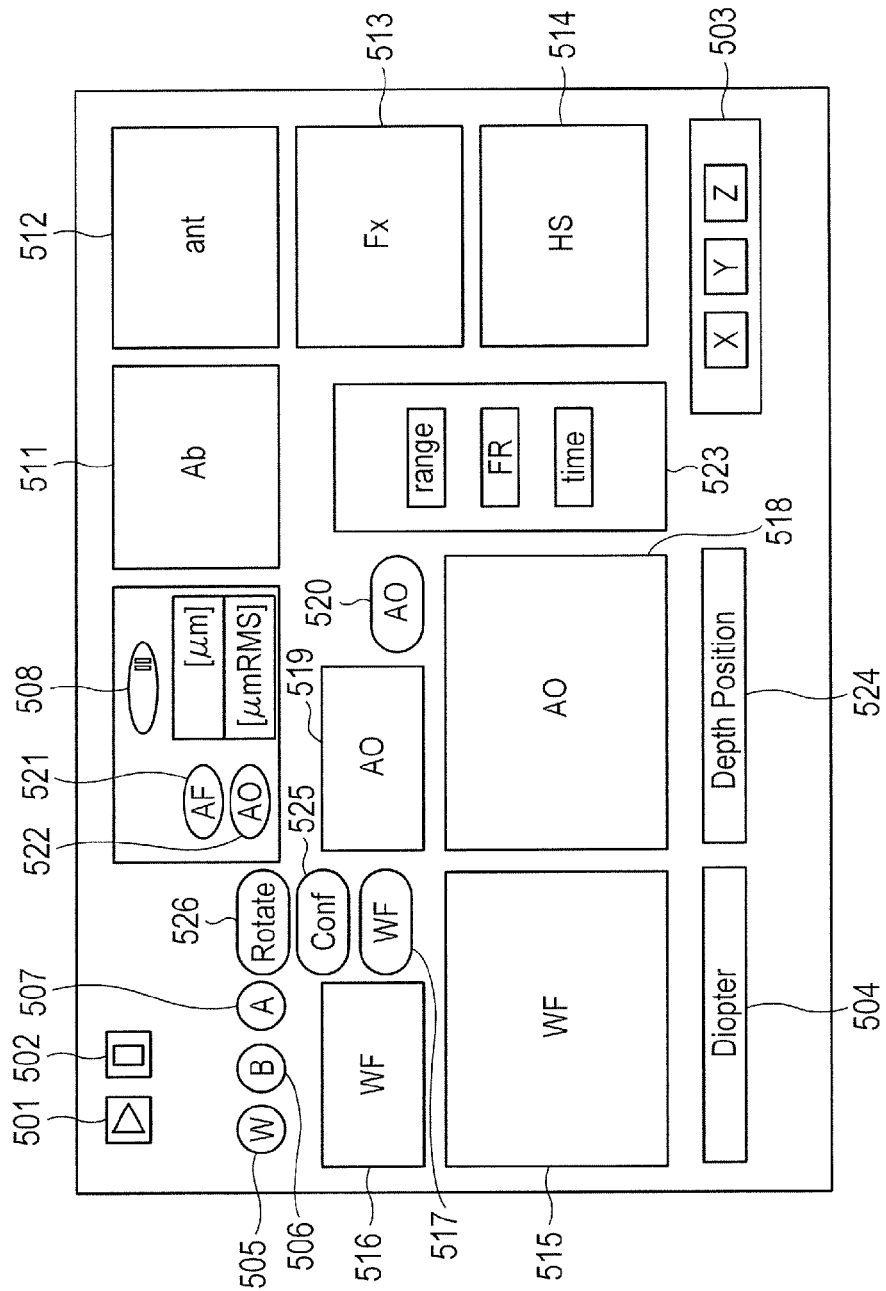
FIG. 5 is a diagram for illustrating the configuration of a control software screen of the SLO apparatus according to the embodiment of the present invention.

The image acquisition procedure is illustrated in FIG. 4. Steps of the procedure are described in detail below. Processing executed in the steps described below is executed by the control PC 106 unless otherwise noted.

<Step S210>

In this step, the AO-SLO apparatus 101 is started up, and the setup status of the AO-SLO apparatus 101 is checked. A user first turns on the power sources of the control PC 106 and the AO-SLO apparatus 101. Then, when control software for measurement is booted, a control software screen illustrated in FIG. 5 is displayed on the liquid crystal monitor 105. At this time, a subject is urged to put a face on the face rest unit 104.

<Step S220>

In this step, an image of an anterior ocular segment is acquired. When an execution button 501 on the control software screen is pressed, an image of an anterior ocular segment is displayed on an anterior ocular segment monitor 512. In the case where the center of a pupil is not correctly displayed at the center of the screen and at a predetermined position of the display screen, the head unit 102 is first moved to a substantially correct position through use of the joystick 107. In the case where further adjustment is required, an electric stage button 503 on the control software screen is pressed to slightly move the chin rest drive unit 109.

<Step S230>

In this step, a WF-SLO image is acquired. In the case where the image of the anterior ocular segment is displayed in a substantially correct state, a WF-SLO image is displayed on a WF-SLO monitor 515. The fixation lamp 256 is set at a center position with a fixation lamp position monitor 513 to guide the line of sight of the eye-to-be-inspected 207 to the center.

Next, the user adjusts a focus adjustment button 504 so as to increase WF-SLO intensity while watching a WF-SLO intensity monitor 516. On the WF-SLO intensity monitor 516, signal strength detected by the WF-SLO unit is displayed in a time series, with the horizontal axis being time and the vertical axis being signal strength. Then, through adjustment of the focus adjustment button 504, the positions of the objective lens 235-10 and the lenses 235-14, 235-16, and 235-18 are adjusted concurrently.

In the case where the WF-SLO image is displayed clearly, a WF-SLO recording button 517 is pressed to store WF-SLO data.

<Step S240>

In this step, a position for acquiring an AO-SLO image is determined. The displayed WF-SLO image is checked, and a position at which an AO-SLO image is intended to be acquired is determined through use of a method described later. Next, the line of sight of the eye-to-be-inspected 207 is guided so that the position for acquiring an AO-SLO image is placed at the center of the WF-SLO monitor 515.

There are two methods of determining the position for acquiring an AO-SLO image. One of the methods is a method involving designating the position of the fixation lamp 256 in the fixation lamp position monitor 513, and the other is a method involving clicking on an intended position on the WF-SLO monitor 515. Pixels on the WF-SLO monitor 515 are associated with the position of the fixation lamp 256 so that the position of the fixation lamp 256 can move automatically to guide the line of sight to an intended position.

After it is confirmed that the position at which an AO-SLO image is intended to be acquired has moved to the center on the WF-SLO monitor 515, the procedure proceeds to the subsequent step.

<Step S250>

In this step, aberrations are compensated. When an aberration measurement button 506 is pressed, the measuring light 206-2 serving as WF-SLO measuring light is blocked, and the shutter of the beacon unit is opened, with the result that the measuring light 206-3 serving as beacon light is radiated to the eye-to-be-inspected 207. A Hartmann image detected by the wavefront sensor 255 is displayed on a wavefront sensor monitor 514. An aberration calculated based on the Hartmann image is displayed on an aberration compensation monitor 511. The aberration is displayed so as to be separated into a defocus component (unit: μm) and the entire aberration amount (unit: μmRMS). In this case, the positions of the objective lens 235-10 for the AO-SLO measuring light and the focusing lens 235-16 for the beacon light are adjusted in Step S230, and hence aberration measurement is ready to be performed in Step S250. Specifically, the return light 208-3 with respect to the measuring light 206-3 passes through the pinhole 298 without being blocked and reaches the wavefront sensor 255.

In this case, when an automatic focus button 521 is pressed, the positions of the objective lens 235-10 and the lenses 235-14, 235-16, and 235-18 are automatically adjusted so that the value of defocus decreases.

Next, when an aberration compensation button 522 is pressed, the spatial light modulator 259 is automatically adjusted so that the aberration amount decreases, and the value of the aberration amount is displayed in real time. In this case, when the value of the aberration amount reaches a threshold value (0.03 μmRMS) or less determined in advance, an AO-SLO measurement button 507 is automatically pressed, and the procedure proceeds to the subsequent step. The threshold value of the aberration amount can be set arbitrarily. Further, in the case where the value of the aberration amount does not reach the threshold value or less, an aberration compensation temporary stop button 508 is pressed to stop the aberration compensation. After that, the AO-SLO measurement button 507 is pressed to cause the procedure to proceed to the subsequent step.

<Step S260>

This step is for acquiring an AO-SLO image, and in the step, only a nonconfocal AO-SLO image picked up in the first image acquisition mode is acquired, or a confocal AO-SLO image picked up in the second image acquisition mode is acquired as well as the nonconfocal image. The premise of the following description is that the nonconfocal image and the confocal image are both acquired, and "AO-SLO image" in the following description refers to both of the images, or one of the images that is selected at the time. When the AO-SLO measurement button 507 is pressed, the measuring light 206-3 serving as the beacon light is blocked and a shutter (not shown) along the optical path of the AO-SLO measuring light 206-1 is opened to radiate the measuring light 206-1 to the eye-to-be-inspected 207. An AO-SLO image already compensated for aberration is displayed on an AO-SLO monitor 518. Further, similarly to the WF-SLO intensity monitor 516, signal strength detected by the AO-SLO unit is displayed in a time series on an AO-SLO strength monitor 519.

In the case where the signal strength is insufficient, the user adjusts focus and a chin rest position while watching the AO-SLO strength monitor 519 so that the signal strength increases.

Further, an image acquisition field angle, a frame rate, and an image acquisition time can be designated by image acquisition condition setting buttons 523.

Further, through adjustment of a depth adjustment button 524, the objective lens 235-10 can be moved in the optical axis direction to adjust the image acquisition range in the depth direction of the eye-to-be-inspected 207. Specifically, an image of an intended layer, such as a photoreceptor cell layer, a nerve fiber layer, or a pigment epithelial layer, which is a typical eye cell, can be acquired.

In the case where the AO-SLO image (for example, confocal image) is clearly displayed, an AO-SLO recording button 520 is pressed to store AO-SLO data. Then, the measuring light 206-1 is blocked. To change the focal depth of the AO-SLO image, a switch is made from one of the division patterns on the partially reflecting mirror 711 to another so that the size of the reflection region in the division pattern is changed, and the switched-to pattern is used to pick up an AO-SLO image again.

<Step S270>

When a nonconfocal mode button 525 (see FIG. 5) is pressed, the screen switches to the display of the nonconfocal AO-SLO image. In the case where an object to be measured has direction dependence on a particular angle, for example, in the case of a particular blood vessel, an angle adjustment unit 526 is used to rotate the light flux dividing prism of the photo-receiving unit to a position suitable for this directionality. Inputting a command to the angle adjustment unit 526 changes the angle of the direction in which a light flux is divided by the light flux dividing prism when a nonconfocal AO-SLO image is acquired based on the rotation angle. The change enables the user to observe a nonconfocal image in which the directionality (angle) is emphasized. In the case where the prism is rotated manually, the AO-SLO apparatus 101 is desirably configured so as to display rotation angle information indicating an angle by which the prism has been rotated manually. To change the focal depth of the nonconfocal image, a switch is made from one of the division patterns on the partially reflecting mirror 711 to another so that the size of the reflection region in the division pattern is changed, and the switched-to pattern is used to pick up an AO-SLO image again. One of the digital values Ia and Ib detected by the photo-receiving unit 700 can be displayed when the nonconfocal image is displayed. The user can also choose to display an image that is based on the pixel value I, which is calculated by the above-mentioned expression from the digital values Ia and Ib as a value that the pixel takes when light is divided in the X-direction. As described above, the angle information about the division direction and a corresponding prism rotation angle is stored in association with an image when the image is stored. While the AO-SLO apparatus 101 here switches between picking up a confocal AO-SLO image and picking up a nonconfocal AO-SLO image, the confocal image and the nonconfocal image may be picked up concurrently. It is useful in this case if a display screen for image acquisition software displays the confocal image and the nonconfocal image simultaneously so that the user can check both while picking up the images.

<Step S280>

The procedure proceeds to Step S240 in the case where the image acquisition position is to be changed, and returns to Step S220 in the case where a switch between the left eye and the right eye is to be made. The procedure proceeds to Step S290 in the case where image acquisition is to be ended.

<Step S290>

When a stop button 502 is pressed, the control software is stopped.

<Image Generation and Analysis Apparatus Configuration>

Figure 6:
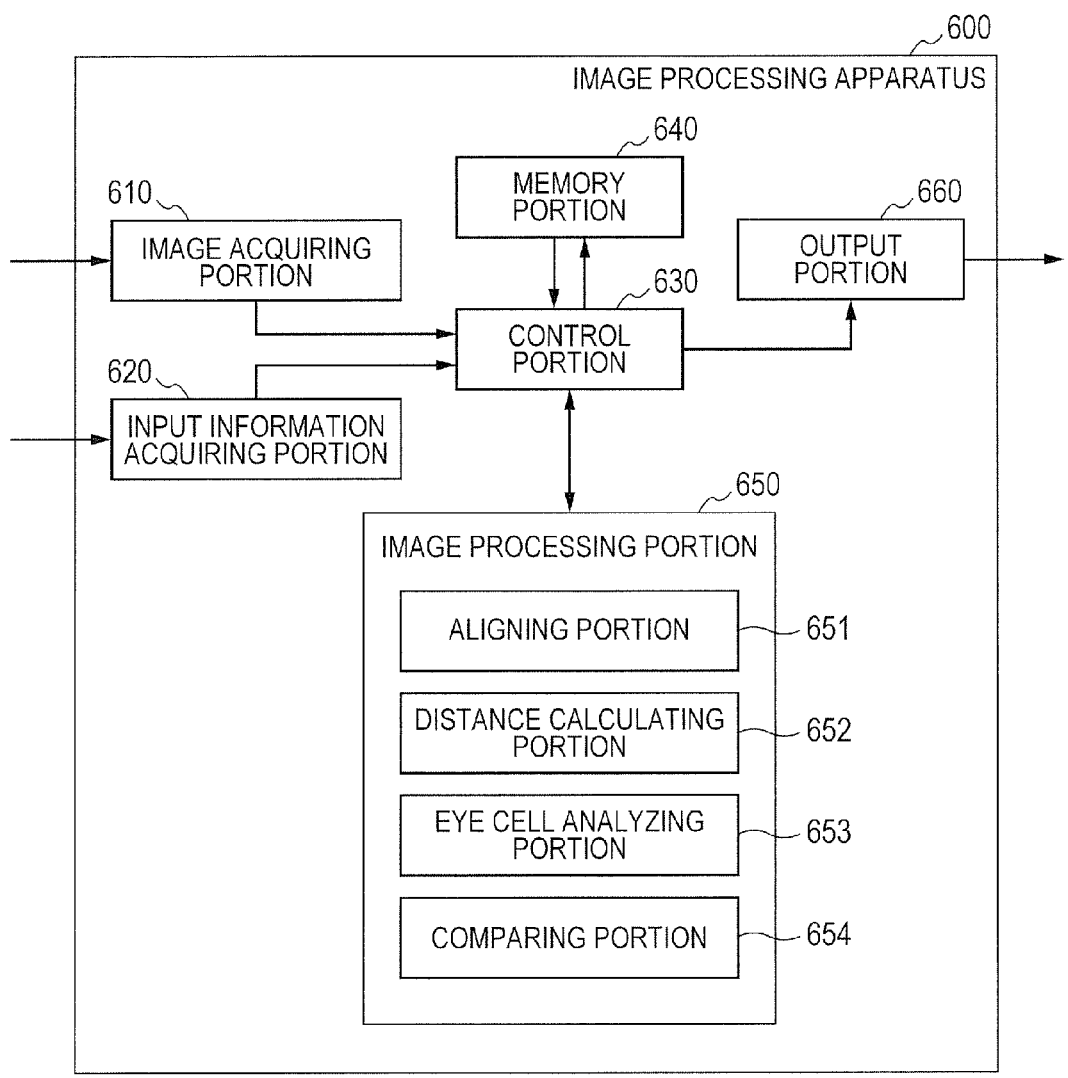
FIG. 6 is a diagram for illustrating the function configuration of an image processing apparatus according to the embodiment of the present invention.

FIG. 6 is a diagram for illustrating the function configuration of the image processing apparatus 600 according to this embodiment. While this embodiment takes as an example an image processing apparatus configured to detect photoreceptor cells, which are a typical example of eye cells, the object to be analyzed is not limited to photoreceptor cells. The present invention is applicable to the analysis of any type of eye cells that can be observed, such as blood vessel wall cells.

In FIG. 6, an image acquiring portion 610 acquires the confocal AO-SLO image, or the nonconfocal AO-SLO image, which has been stored in Step S260, and a prism rotation direction corresponding to the light flux division direction in the nonconfocal image. The acquired confocal AO-SLO image or nonconfocal AO-SLO image, and the light flux division direction are stored via a control portion 630 in a memory portion 640, which is a recording unit. An input information acquiring portion 620 acquires an input from the user. An image processing portion 650 includes a alignment portion 651, a distance calculating portion 652, an eye cell analyzing portion 653, and a comparing portion 654. The image processing portion 650 performs alignment to position a plurality of acquired nonconfocal AO-SLO images in relation to one another and obtain the relative position in each confocal AO-SLO image or each nonconfocal AO-SLO image. The image processing portion 650 also obtains the distance of an image analysis target region from a macula, based on a positional relationship in a nonconfocal AO-SLO image where macula detection is conducted and a nonconfocal AO-SLO image that is a target of image analysis. The image processing portion 650 performs photoreceptor cell analysis on which the obtained distance from the macula is reflected, and calculates reference values for the inspection result of the inspected eye, such as density. The image processing portion 650, in particular, the comparing portion 654, compares acquired data to normal eye data stored in the memory portion 640, and generates a graph or image that clearly indicates the result of the comparison. An output portion 660 outputs the calculated reference values to the monitor or the like, and also outputs a processing result stored in the memory portion 640 to a database.

<Processing Procedure of Image Processing Apparatus>

Figure 10:
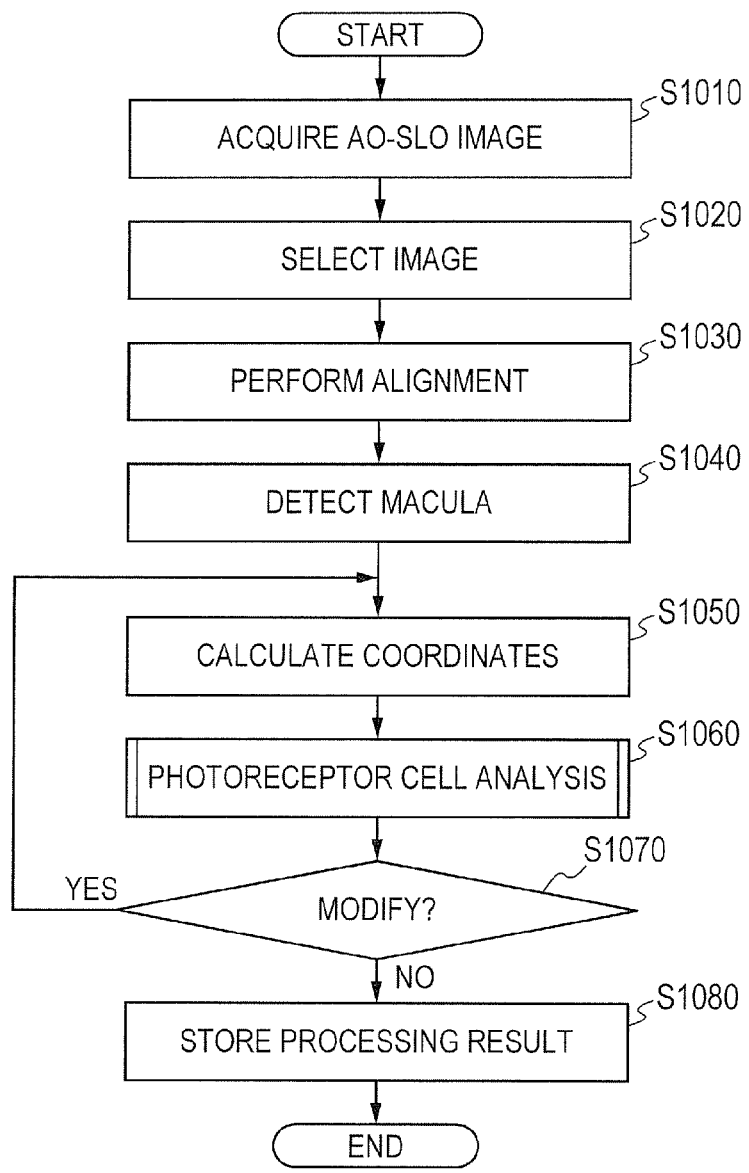
FIG. 10 is a diagram for illustrating a processing procedure that is executed on the image processing apparatus according to the embodiment of the present invention.

A processing procedure executed by the image processing apparatus 600 of this embodiment is described next with reference to a flow chart of FIG. 10.

<Step S1010>

In Step S1010, the image acquiring portion 610 acquires a WF-SLO image of the fundus of an eye to be inspected as well as a plurality of confocal AO-SLO images of the fundus, or a plurality of nonconfocal AO-SLO images of the fundus, and a nonconfocal image, through the SLO apparatus connected to the image processing apparatus 600. The acquired images as well as data related to image forming which includes intensity signals for forming images and scanning signals are stored in the memory portion 640 as image data. The light flux division direction of the return light 208-1 that has been used for the acquired images is also obtained and stored in the memory portion 640 via the control portion 630. The control portion 630 stores the image acquisition modes described above in the memory portion 640 as well in association with the image data.

In the case where a confocal AO-SLO image and a nonconfocal AO-SLO image are picked up simultaneously, the image data and other pieces of relevant information are similarly stored for the confocal AO-SLO image in Step S1010.

<Step S1020>

In Step S1020, the information acquiring portion 620 selects a reference frame out of frames that make up a nonconfocal AO-SLO image stored in the memory portion 640.

One nonconfocal AO-SLO image is made up of a plurality of frames that are picked up images of the same place. However, the image acquisition position shifts due to slight movement of the fixed line of sight of the eye to be inspected, thereby causing distortions in the frames. Out of such frames, the user selects as the reference frame a frame that has little distortion and fine image acquisition conditions.

While the case where the user selects the reference frame is described here, the reference frame may be selected by way of software. For example, a mean value or dispersion of luminance may be calculated to select frame that is high in mean value or dispersion. Another possible way is to select a frame having a definite ring structure, which indicates the presence of photoreceptor cells, by performing frequency analysis.

In the case where a confocal AO-SLO image and a nonconfocal AO-SLO image are picked up simultaneously, the reference frame can be the confocal AO-SLO image.

The reference frame selected for each AO-SLO image in this manner is stored in the memory portion 640 via the control portion 630.

<Step S1030>

In Step S1030, the alignment portion 651 performs alignment to position a plurality of nonconfocal AO-SLO images acquired by the SLO apparatus and stored in the memory portion 640 in relation to one another. The alignment uses the reference frame selected for each nonconfocal AO-SLO image. In the alignment, the alignment portion 651 also calculates the amount of movement of each site at which an AO-SLO image has actually been acquired, with respect to the WF-SLO image. The calculated movement amount is stored in the memory portion 640 via the control portion 630.

In the case where the reference frame selected in Step S1020 is the confocal AO-SLO image, the alignment of nonconfocal AO-SLO images may be executed by reflecting the result of alignment with the use of the confocal AO-SLO image on the nonconfocal AO-SLO images. After the alignment is finished, the plurality of nonconfocal images are laid on top of one another to generate a superimposed image.

The thus acquired superimposed image of nonconfocal AO-SLO images is stored in the memory portion 640 via the control portion 630. The superimposed image is displayed on the monitor or the like via the output portion 660, and then the procedure returns to Step S1030.

<Step S1040>

In Step S1040, the input information acquiring portion 620 obtains the position of the center of the macula in the superimposed image generated in Step S1030. The detected macula center position is stored in the memory portion 640 via the control portion 630.

<Step S1050>

In Step S1050, the distance calculating portion 652 calculates the movement amount calculated in Step S1030, i.e., the amount of movement of each nonconfocal AO-SLO image, which is an actual image acquisition site, with respect to the WF-SLO image. The distance calculating portion 652 also calculates, for each nonconfocal AO-SLO image, the distance from the macula position obtained in Step S1040 to the nonconfocal image.

Specifically, the distance calculating portion 652 obtains, for each nonconfocal AO-SLO image, which is an actual image acquisition site, center coordinates in the nonconfocal image with the macula set as the origin of the coordinate system, the top side of the superimposed image as the Y-axis direction, and the right side of the superimposed image as the X-axis direction. The thus obtained coordinates in each nonconfocal AO-SLO image are referred to as macula coordinates. This is expressed as Di-M when the movement amount of an image i which is the movement amount obtained for each nonconfocal AO-SLO image in Step S1030 is given as a vector Di, and the macula position obtained in Step S1040 is given as a vector M from the center of the WF-SLO image. When the center coordinates in the nonconfocal AO-SLO image i are given as (Xi, Yi), a distance Ri from the macula thereof can be obtained as follows.

$$R_i = \sqrt{X_i^2 + Y_i^2}$$

The obtained macula coordinates and distance from the macula in each nonconfocal AO-SLO image are stored in the memory portion 640 via the control portion 630.

<Step S1060>

In Step S1060, the eye cell analyzing portion 653 performs photoreceptor cell analysis on the nonconfocal AO-SLO images acquired in Step S1010 which are actual image acquisition sites. As described later, the eye cell analyzing portion 653 analyzes stored image data that has been generated from outputs of the detectors and scanning signals of the scanner, based on the image data and a light flux division direction that is associated with the image data, the light flux division direction being a direction in which a light flux has been divided by the light flux dividing unit to acquire the image data.

Figure 11:
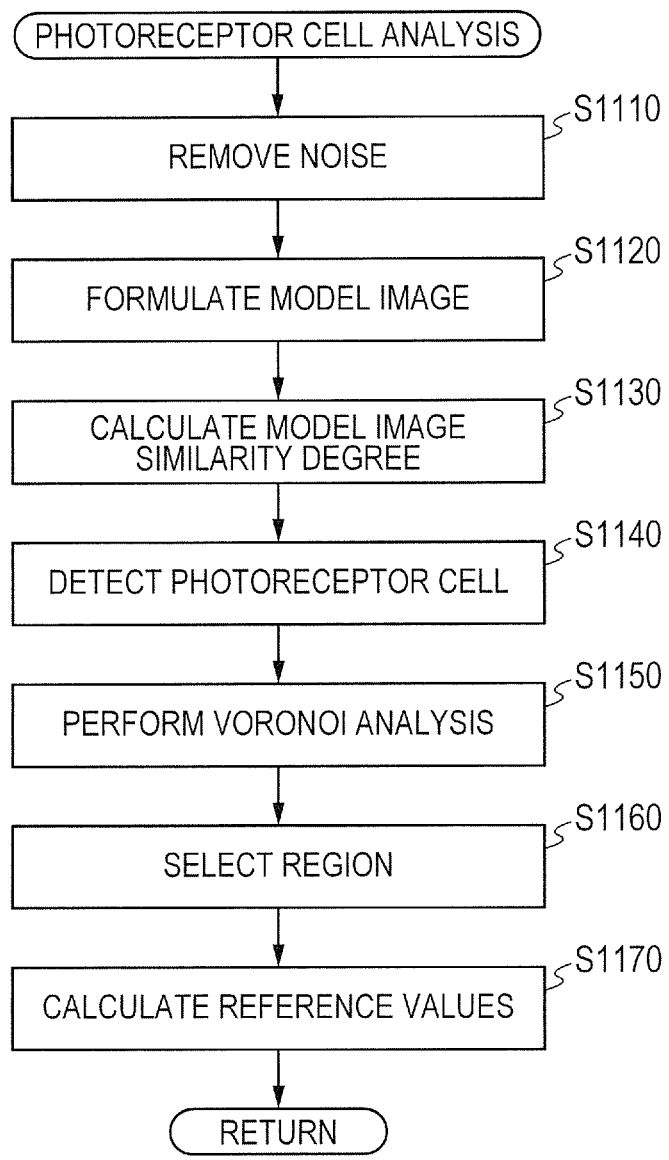
FIG. 11 is a diagram for illustrating details of photoreceptor cell analyzing processing, which is executed in the processing of FIG. 10.

FIG. 11 is a flow chart for illustrating details of the photoreceptor cell analysis. In this embodiment, the degree of similarity between a prepared photoreceptor cell model image and an acquired AO-SLO image or the like is obtained, and photoreceptor cells in the acquired image are detected by using the degree of similarity. Nonconfocal AO-SLO images have directionality in terms of image characteristics such as sharpness. This embodiment takes the directionality of a nonconfocal AO-SLO image into consideration, and uses a model image that has a contrast gradient component of which the directionality matches the directionality of the nonconfocal AO-SLO image. In other words, image data is analyzed based on the directionality of image characteristics which corresponds to the division direction of nonconfocal light. More specifically, in the case where return light is divided so that the division direction of nonconfocal light is left to right (the light shielding region 713 stretches in the top-to-bottom direction), and the image to be analyzed is generated based on light that is on the right side as a result of the division, for example, the image when displayed looks sharp on the left side if the image is of a site that runs in the top-to-bottom direction in the image acquisition region. It is therefore preferred to use image characteristic on the left side of the image preferentially when light created by the division is one on the right side.

The procedure of the analysis is described in detail below.

<Step S1110>

In Step S1110, the eye cell analyzing portion 653 executes pre-processing of photoreceptor cell analysis based on the reference frame obtained in Step S1020. An image acquired in this embodiment is not always a nonconfocal image picked up in the first image acquisition mode, and is a confocal image picked up in the second image acquisition mode in some cases. The second image acquisition mode uses light that is at the central portion of the return light, whereas the first image acquisition mode uses light that is outside the central portion. It is therefore necessary to determine the type of an image to be actually processed, in other words, which of a nonconfocal image and a confocal image is to be processed. The determination can be made by selecting a detector from which a signal to be used is obtained, in the case where the image has actually been acquired. In the case where image data stored in the memory portion in advance is referred to, each piece of image data is associated with information of a detector from which a signal used to form the image data has been output.

In the case where the image to be processed is a nonconfocal image and the reference frame selected in Step S1020 is a confocal AO-SLO image, pre-processing is executed by using as the reference frame a frame of a nonconfocal AO-SLO image that has been picked up at the same time as the confocal AO-SLO image. The premise of the following description of processing steps is that the image to be processed is a nonconfocal image. A description on processing steps that are executed when the image to be processed is a confocal image picked up in the second image acquisition mode is omitted because confocal images can be processed by a known method of image feature point extraction. It is preferred in the case of confocal images to acquire an image that has no directionality. It is therefore preferred to use feature points having no directionality in image data when feature points are extracted from confocal images.

The pre-processing can be executed by a plurality of methods. Here, noise removal by frequency analysis is described. Specifically, frequency conversion is performed on the reference frame and, after a filter configured to remove high frequency is applied, inverse transform is performed. A cutoff value at which high frequency is removed as noise is based here on a known fact that the size of a photoreceptor cell is about 2 μm near a macula, where the photoreceptor cell size is minimum (the density of photoreceptor cells is highest). Vibrations having a shorter cycle than 2 μm are therefore removed. It is also a known fact that the photoreceptor cell density drops as the distance from a macula increases, and the cutoff frequency is accordingly varied based on the distance calculated in Step S1050. For example, the cutoff frequency is suited to the distance from a macula by setting the cutoff frequency to 2 μm in the central portion of a macula, increasing the cutoff frequency by 1 μm for every increment of 0.5 mm in distance from the macula in a range between the center of the macula and 1.0 mm from the center of the macula, and setting the cutoff frequency to 4 μm (fixed) at a point that is away from the macula by 1.0 mm or more.

Another method of noise removal is to superimpose a plurality of frames acquired as nonconfocal AO-SLO images. Specifically, registration processing through affine transform or the like is performed on a plurality of frames of each nonconfocal AO-SLO image, and then mean value processing is executed for a region that corresponds to the reference frame. The precision of this method is dependent on the precision of the registration processing. After the registration processing is executed, the above-mentioned processing of removing high frequency components by frequency conversion is executed. Noise removal may use other common processing methods, and is not limited to what has been described. An image acquired in this manner is referred to as "pre-processed image".

<Step S1120>

As described above, a nonconfocal image that is usually generated from two received-light signals that are created by dividing a light flux generally has characteristics in the direction in which the light flux has been divided, in other words, has directionality of image characteristics. A model image to be used for similarity degree calculation therefore preferably has a contrast gradient component in a direction that substantially matches the light flux division direction in the nonconfocal image, in order to analyze the image effectively by utilizing the directionality of image characteristics. The model image and a filter, which is described later, are stored in the memory portion 640, which is a storing unit. The model image for similarity degree calculation can be formulated by a plurality of methods. In this embodiment, the eye cell analyzing portion 653 uses in Step S1120 a model image that uses the first derivation of a Gaussian function, as a model image for similarity degree calculation that has a contrast gradient component in the same direction as a light flux division direction stored in the memory portion 640 for photoreceptor cell analysis.

When the top side of a model image is set as a T-axis direction, the right side of the model image is set as an S-axis direction, and coordinates in the model image are given as (s, t), the first derivation of a Gaussian function can be obtained as follows.

$$G(s, t) = \frac{\partial}{\partial s}\left(\frac{1}{2\pi\sigma^2}\exp\left(-\frac{s^2+t^2}{2\sigma^2}\right)\right)$$

In this expression, a spread 6σ of the Gaussian function and the size of the model image correspond to the size of a photoreceptor cell, and the photoreceptor cell size is known to increase as the distance from a macula grows. The value of σ, namely, the relative size of the model image is therefore determined automatically based on the distance obtained in Step S1050. Specifically, an approximate expression of a relationship between the photoreceptor cell diameter and the distance from a macula is calculated, and the distance obtained in Step S1050 is used to calculate the photoreceptor cell diameter. The value of σ is calculated by regarding the photoreceptor cell diameter as a value equal to the spread 6σ of the Gaussian function, and the size of the model image is determined automatically as that of a square having the length of the calculated photoreceptor cell diameter on a side. In other words, the size of the model image relative to a photoreceptor cell size of image data actually stored is calculated based on the calculated distance. The model image and the like are determined based on the division direction of the outer light flux described above.

The photoreceptor cell size, which is calculated here automatically based on the distance from a macula, may instead be determined by a method in which the user manually inputs distance information or a method in which the user manually inputs the photoreceptor cell size. Alternatively, the pre-processed image may be used to determine the photoreceptor cell size automatically from the pre-processed image. For example, the photoreceptor cell size may be determined by performing frequency conversion on the pre-processed image and using a frequency component.

The above-mentioned expression is an expression for generating a model image when the light flux division direction of the photo-receiving unit in the SLO apparatus is the main scanning direction. Needless to say, when the light flux division direction in a nonconfocal image that is stored in the memory portion 640 is not the main scanning direction, the model image needs to be rotated in a corresponding direction. While model image formulation by the first derivation of a Gaussian function has been described here, a filter having a contrast gradient component in the same direction as the light flux division direction in a nonconfocal image may be created and applied. For example, a common edge extraction filter such as a Sobel filter, which is a typical filter used to extract a contrast gradient component, may be used. The present invention is not limited to the methods described above, and any method can be employed as long as the method involves processing in which the division direction is associated with the direction of edge extraction. While this embodiment focuses on the contrast gradient component as the characteristics of a model image to be used, it is sufficient if some gradient component of the model image such as contrast, luminance, or sharpness, or a combination of the gradient components, has particular directionality.

<Step S1130>

In Step S1130, the eye cell analyzing portion 653 calculates the degree of similarity between the pre-processed image acquired in Step S1110 and the model image formulated in Step S1120. The degree of similarity can be calculated by a plurality of methods. Here, similarity degree calculation by normalized cross-correlation is described. A pre-processed image luminance at coordinates (x, y) in the pre-processed image and a model image luminance at the coordinates (x, y) in the model image are given as I(x, y) and M(x, y), respectively, and the mean luminance of the former and latter are expressed as follows.

$\bar{I}, \bar{M}$

Then, a normalized cross-correlation image C (x, y) can be obtained as follows.

$$C(x, y) = \frac{\sum_i \sum_j ((I(x+i, y+j) - \bar{I})(M(i, j) - \bar{M}))}{\sqrt{\sum_i \sum_j (I(x+i, y+j) - \bar{I})^2 \sum_i \sum_j (M(i, j) - \bar{M})^2}}$$

The thus acquired image that indicates the degree of similarity to the model image is referred to as "model similarity degree image". In the case where a filter is created in Step S1120, filter processing is performed on the pre-processed image, which has been acquired in Step S1110, and the acquired image is used in the subsequent steps.

<Step S1140>

In Step S1140, the eye cell analyzing portion 653 conducts photoreceptor cell detection in the model similarity degree image acquired in Step S1130.

The eye cell analyzing portion 653 first detects a local maximum value of the luminance of the model similarity degree image. In the case where the distance between points detected as the local maximum value is smaller than a size that a photoreceptor cell is theoretically known to have, the eye cell analyzing portion 653 determines that this is due to the influence of noise, and executes processing of integrating the detection points. The photoreceptor cell size used here is calculated, as in Step S1110, based on the distance calculated in Step S1050 which is the distance of a nonconfocal AO-SLO image (actual image acquisition site) that is an image analysis target from a macula. This way, detection of higher precision is accomplished.

The photoreceptor cell detection given here is an example. The method of detection is not limited to the one described above, and there are various possible methods that can be used. The various methods include, for example, one in which only pixels having a luminance value higher than a threshold are selected and the barycenter of a region where the selected pixels are linked is obtained. Another method of detection involves calculating the feature amount of a small region and using the technique of pattern recognition. Specifically, a Gabor feature amount is calculated for a small region that is 11 pixels by 11 pixels, for example. Gabor feature vectors obtained from a plurality of small regions each of which contains a detection point regarded as a photoreceptor cell at the center and a plurality of small regions each of which does not contain the detection point are fed to a support vector machine for learning. A Gabor feature amount is calculated for a small region that is a new target of pattern recognition, and the result of the leaning is used to determine whether or not the center of the new small region is a photoreceptor cell.

The detection by software described above may be used in combination with manual modification by the user, or the user may conduct detection manually from the beginning. The input information acquiring portion 620 in this case obtains the position of a detection point that has been detected in Step S1140 and then modified by the user.

<Step S1150>

In Step S1150, the eye cell analyzing portion 653 performs Voronoi analysis on the detection point detected in Step S1140.

Specifically, for every detection point detected in Step S1140, a Voronoi region belonging to the detection point is calculated by dividing a region in the image along a perpendicular bisector of detection points that are in the vicinity of each other.

<Step S1160>

In Step S1160, the eye cell analyzing portion 653 selects a region for which reference values for the results of analysis of Step S1140 and Step S1150 are to be calculated. The reference values here mean ones that are used to determine whether an eye being inspected has an anomaly when the eye being inspected is compared to a normal eye as described above.

To select the region, an area of a certain size may be selected out of the pre-processed image, or a selection region may be set for each detection point. For example, for each detection point, a circle having a diameter of 20 μm and centered about the detection point may be set and the inside of the circle may be considered as a region corresponding to the detection point. The measure of selection is not limited to detection points, and a region may be set for every given number of pixels that leave a suitable gap between one region and another. For example, pixels are selected at ten-pixel intervals across and down and, also in this case, a circle having a diameter of 20 μm can be set for each selected pixel in order to use a region inside of the circle as a selected region.

The distance of the selected region from a macula is calculated. The position of each AO-SLO image, which is an actual image acquisition site, from the macula has already been calculated in Step S1050. The distance of the center of the selected region from the macula is calculated based on the position of the selected region in the AO-SLO image.

<Step S1170>

In Step S1170, the eye cell analyzing portion 653 calculates the reference values for the region selected in Step S1160, based on the results obtained in Step S1140 and Step S1150.

Examples of the reference values include the number of detection points obtained in Step S1140, a density that is calculated by dividing the number of detection points by the area, the distance to the closest detection point obtained in Step S1150, and the proportion of Voronoi regions that are hexagonal to all Voronoi regions.

The results of the photoreceptor cell analysis and the obtained reference values are stored in the memory portion 640 via the control portion 630, and then the processing returns to Step S1060.

<Step S1070>

In Step S1070, the input information acquiring portion 620 acquires the user's decision about whether or not to modify the analysis results presented in Step S1060. The modification by the user is made to the alignment of AO-SLO images executed in Step S1030 and the macula detection conducted in Step S1040.

Specifically, when determining that the alignment of an AO-SLO image in Step S1030 has been done incorrectly, the user can change the position of the AO-SLO image. The user can also change the macula position determined in Step S1040.

In the case where the user decides not to make modifications, the procedure proceeds to Step S1080. In the case where the user has made modifications, the procedure returns to Step S1050 to calculate the distance again based on the modified macula position and the modified AO-SLO image positions, and the subsequent processing steps are executed.

<Step S1080>

In Step S1080, the control portion 630 stores, in a database, the calculated reference values, the comparison result, and other processing results stored in the memory portion 640.

As has been described above, a nonconfocal image generated from received-light signals that result from dividing a light flux has directionality of image characteristics. According to the present invention, photoreceptor cells can be detected with a higher precision by using a model image for similarity degree calculation that has a contrast gradient component in a direction substantially matching the direction of the light flux division in an analysis of the nonconfocal image having the directionality. In addition, when reference values are calculated through an analysis of a plurality of nonconfocal AO-SLO images acquired with the SLO apparatus, the positional relationship with a macula that is not included in the same AO-SLO image can be taken into account in the analysis.

Other Embodiments

The embodiment described above deals with a detection method in photoreceptor cell analysis. Also in the detection of a blood vessel or a tumor, an edge portion of the object to be detected itself or of a structure or the like can be detected by performing calculation in which the light flux division direction in a nonconfocal image is associated with the direction of a contrast gradient component of a filter or a model image for similarity degree calculation.

Further, the present invention is not limited to the above-mentioned embodiment, and can be embodied with various changes and modifications without departing from the spirit of the present invention. For instance, although the object to be inspected is an eye in the above-mentioned embodiment, the present invention can be applied to an object to be measured other than an eye, such as skin or an organ. In this case, the present invention includes an aspect as medical devices, such as an endoscope, other than ophthalmic apparatus. Thus, it is desired that the present invention be grasped as an inspection apparatus exemplified as an ophthalmic apparatus or a method of operating an inspection apparatus, and an eye to be inspected be grasped as one aspect of an object to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-094244, filed May 1, 2015, and Japanese Patent Application No. 2016-033071, filed Feb. 24, 2016, which are hereby incorporated by reference herein in their entirety.

What is claimed is:

1. An inspection apparatus comprising:
a measurement optics system configured to scan an object to be inspected with measuring light from a light source;
a dividing unit, which is arranged at a position conjugate with the object to be inspected, and which is configured to divide return light, being the measuring light returning from the object to be inspected, into a plurality of light beams;
a photo-receiving unit configured to receive the plurality of light beams obtained by the division;
a recording unit configured to record (a) image data of the object to be inspected, the image data being obtained by using a plurality of intensity signals output by the photo-receiving unit, and (b) a division direction in which the return light is divided, the image data being associated with the division direction; and
an analysis unit configured to analyze the image data using the associated division direction.

2. An inspection apparatus according to claim 1, wherein the recording unit is configured to record a model image for use in the analysis of the image data, and
wherein the analysis unit is configured to analyze the image data by using the model image that is determined using the division direction of the return light.

3. An inspection apparatus according to claim 1, wherein the recording unit is configured to record at least one of a model image or a filter that comprises a contrast gradient component having at least directionality for the analysis of the image data, and
wherein the analysis unit is configured to analyze the image data by using at least one of the model image or the filter that comprises the contrast gradient component having directionality that matches the division direction recorded in association with the image data.

4. An inspection apparatus according to claim 1, wherein the dividing unit is variable in the division direction of the return light.

5. An inspection apparatus according to claim 1, further comprising:
another dividing unit, which is configured to take out light at a central portion of the return light;
another photo-receiving unit, which is configured to receive the light at the central portion of the return light; and
a generating unit configured to generate the image data of the object to be inspected using an intensity signal output by the another photo-receiving unit,
wherein the dividing unit divides light in a portion of the return light that is outside the central portion into the plurality of light beams, and
wherein the generating unit generates the image data of the object to be inspected, using the plurality of intensity signals.

6. An inspection apparatus according to claim 1, further comprising:
another dividing unit, which is configured to take out light at a central portion of the return light; and
another photo-receiving unit, which is configured to receive the light at the central portion of the return light,
wherein the image data of the object to be inspected is generated by a first image acquisition mode of using the plurality of intensity signals and a second image acquisition mode of using an intensity signal output by the another photo-receiving unit.

7. An inspection apparatus according to claim 6, further comprising a determining unit configured to determine which of the first image acquisition mode and the second image acquisition mode has been used to acquire the image data to be analyzed,
wherein the analysis unit is configured to, when it is determined by the determining unit that the second image acquisition mode has been used to acquire the image data, perform an analysis in which feature points without directionality are extracted from the image data.

8. An inspection apparatus according to claim 1, wherein the object to be inspected comprises an eye to be inspected,
wherein the recording unit is configured to record the image data and information about a distance between an image acquisition site of a fundus of the eye to be inspected and a macula portion, the image data being associated with the information, and wherein the analysis unit is configured to analyze the image data by using the associated information about the distance.

9. An inspection apparatus according to claim 1, wherein the analysis unit is configured to analyze the image data using directionality of image characteristics that corresponds to the division direction.

10. An image processing apparatus comprising:
an obtaining unit configured to obtain a nonconfocal image of an eye to be inspected, the nonconfocal image being generated by using a plurality of intensity signals obtained by receiving a plurality of light beams obtained by dividing return light from the eye to be inspected;
a recording unit configured to record (a) the nonconfocal image, and (b) a division direction in which the return light is divided, the nonconfocal image being associated with the division direction; and
an analysis unit configured to analyze the nonconfocal image using the associated division direction.

11. An image processing apparatus according to claim 10, wherein the analysis unit is configured to analyze the nonconfocal image by using at least one of a model image or a filter that comprises a gradient component that matches the division direction.

12. A method of operating an inspection apparatus, the method comprising:
dividing, at a position conjugate with an object to be inspected, return light, being measuring light that has been scanned on the object to be inspected and returns from the object to be inspected, into a plurality of light beams;
receiving, by a photo-receiving unit, the plurality of light beams obtained by the division;
recording (a) image data of the object to be inspected, the image data being obtained by using a plurality of intensity signals output by the photo-receiving unit, and (b) a division direction in which the return light is divided, the image data being associated with the division direction; and
analyzing the image data using the associated division direction.

13. A method of operating an inspection apparatus according to claim 12, wherein the recording comprises recording a model image for use in the analysis of the image data, and
wherein the analyzing comprises analyzing the image data by using the model image that is determined using the division direction of the return light.

14. A method of operating an inspection apparatus according to claim 12, wherein the recording comprises recording at least one of a model image or a filter that comprises a contrast gradient component having at least directionality for the analysis of the image data, and
wherein the analyzing comprises analyzing the image data by using at least one of the model image or the filter that comprises the contrast gradient component having directionality that matches the division direction recorded in association with the image data.

15. A method of operating an inspection apparatus according to claim 12, wherein the object to be inspected comprises an eye to be inspected,
wherein the recording comprises recording the image data and information about a distance between an image acquisition site of a fundus of the eye to be inspected and a macula portion, the image data being associated with the information, and wherein the analyzing comprises analyzing the image data by using the associated information about the distance.

16. A method of operating an inspection apparatus according to claim 12, wherein the analyzing comprises analyzing the image data using directionality of image characteristics that corresponds to the division direction.

17. An image processing method comprising:
obtaining a nonconfocal image of an eye to be inspected, the nonconfocal image being generated by using a plurality of intensity signals obtained by receiving a plurality of light beams obtained by dividing return light from the eye to be inspected;
recording (a) the nonconfocal image and (b) a division direction in which the return light is divided, the nonconfocal image being associated with the division direction; and
analyzing image data of the nonconfocal image using the associated division direction.

18. An image processing method according to claim 17, wherein the analyzing comprises analyzing the nonconfocal image by using at least one of a model image or a filter that comprises a gradient component that matches the division direction.

19. A non-transitory computer-readable storage medium having recorded thereon a program for causing a computer to execute the method of operating an inspection apparatus according to claim 12.

20. A non-transitory computer-readable storage medium having recorded thereon a program for causing a computer to execute the image processing method according to claim 17.

21. An inspection apparatus comprising:
a measurement optics system configured to scan an object to be inspected with measuring light from a light source;
a dividing unit, which is arranged at a position conjugate with the object to be inspected, and which is configured to divide return light, being the measuring light returning from the object to be inspected, into a plurality of light beams;
a photo-receiving unit configured to receive the plurality of light beams obtained by the division; and
a recording unit configured to record (a) image data of the object to be inspected, the image data being obtained by using a plurality of intensity signals output by the photo-receiving unit, and (b) division information relating to the division, the image data being associated with the division information.

22. An inspection apparatus according to claim 21, further comprising an analysis unit configured to analyze the image data using the associated division information.

23. An inspection apparatus according to claim 21, wherein the dividing unit is variable in the division information of the return light.

24. An inspection apparatus according to claim 21, further comprising:
another dividing unit, which is configured to take out light at a central portion of the return light;
another photo-receiving unit, which is configured to receive the light at the central portion of the return light; and
a generating unit configured to generate the image data of the object to be inspected using on an intensity signal output by the another photo-receiving unit,
wherein the dividing unit divides light in a portion of the return light that is outside the central portion into the plurality of light beams, and wherein the generating unit generates the image data of the object to be inspected, using the plurality of intensity signals.

25. A method of operating an inspection apparatus comprising:
   dividing, at a position conjugate with the object to be inspected, return light, being measuring light that has been scanned on the object to be inspected and returns from the object to be inspected, into a plurality of light beams;
   receiving, by a photo-receiving unit, the plurality of light beams obtained by the division; and
   recording (a) image data of the object to be inspected, the image data being obtained by using a plurality of intensity signals output by the photo-receiving unit, and (b) division information relating to the division, the image data being associated with the division information.

26. A non-transitory computer-readable storage medium having recorded thereon a program for causing a computer to execute the image processing method according to claim 25.

27. An image processing apparatus comprising:
   an obtaining unit configured to obtain a nonconfocal image of an eye to be inspected, the nonconfocal image being generated by using a plurality of intensity signals obtained by receiving a plurality of light beams obtained by dividing return light from the eye to be inspected; and
   a recording unit configured to record (a) the nonconfocal image and (b) division information relating to the division, the nonconfocal image being associated with the division information.

28. An image processing apparatus according to claim 27, further comprising an analysis unit configured to analyze the nonconfocal image using the associated division information.

29. An image processing apparatus according to claim 28, wherein the analysis unit is configured to analyze the nonconfocal image using at least one of a model image or a filter that comprises a gradient component that matches the division information.

30. An image processing method comprising:
   obtaining a nonconfocal image of an eye to be inspected, the nonconfocal image being generated by using a plurality of intensity signals obtained by receiving a plurality of light beams obtained by dividing return light from the eye to be inspected; and
   recording (a) the nonconfocal image and (b) division information relating to the division, the nonconfocal image being associated with the division information.

31. A non-transitory computer-readable storage medium having recorded thereon a program for causing a computer to execute the image processing method according to claim 30.

* * * * *